(12) United States Patent
Adebar et al.

(10) Patent No.: US 12,004,830 B2
(45) Date of Patent: Jun. 11, 2024

(54) SYSTEMS AND METHODS FOR MONITORING PATIENT MOTION DURING A MEDICAL PROCEDURE

(71) Applicant: INTUITIVE SURGICAL OPERATIONS, INC., Sunnyvale, CA (US)

(72) Inventors: Troy K. Adebar, Mountain View, CA (US); Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 663 days.

(21) Appl. No.: 16/638,660

(22) PCT Filed: Aug. 14, 2018

(86) PCT No.: PCT/US2018/046685
§ 371 (c)(1),
(2) Date: Feb. 12, 2020

(87) PCT Pub. No.: WO2019/036456
PCT Pub. Date: Feb. 21, 2019

(65) Prior Publication Data
US 2020/0297442 A1 Sep. 24, 2020

Related U.S. Application Data

(60) Provisional application No. 62/546,366, filed on Aug. 16, 2017.

(51) Int. Cl.
*A61B 34/10* (2016.01)
*A61B 34/20* (2016.01)
(Continued)

(52) U.S. Cl.
CPC .............. *A61B 34/37* (2016.02); *A61B 34/10* (2016.02); *A61B 34/20* (2016.02);
(Continued)

(58) Field of Classification Search
CPC ................ A61B 1/00006; A61B 1/267; A61B 2034/102; A61B 2034/105;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

CN 104736092 A 6/2015
CN 105208960 A 12/2015
(Continued)

OTHER PUBLICATIONS

Office Action dated Feb. 14, 2022 for Chinese Application No. 201880051752.7 filed Aug. 14, 2018, 32 pages.
(Continued)

*Primary Examiner* — Christopher L Cook
(74) *Attorney, Agent, or Firm* — Haynes & Boone, LLP

(57) ABSTRACT

A method of controlling an elongate instrument during a medical procedure involving motion of the elongate instrument relative to a patient is provided. The method includes generating, by a control system, a first model of the elongate instrument, and generating, by the control system, a second model of the elongate instrument based on a reference pose of the elongate instrument. The method further includes comparing, by the control system, the first model with the second model and determining, by the control system, a state of a system configuration based on the comparison.

20 Claims, 16 Drawing Sheets

(51) Int. Cl.
  *A61B 34/37* (2016.01)
  *A61B 34/30* (2016.01)
  *A61B 90/00* (2016.01)
(52) U.S. Cl.
  CPC ... *A61B 2034/102* (2016.02); *A61B 2034/105* (2016.02); *A61B 2034/2061* (2016.02); *A61B 2034/301* (2016.02); *A61B 2090/062* (2016.02)
(58) Field of Classification Search
  CPC ...... A61B 2034/2061; A61B 2034/301; A61B 2090/062; A61B 34/10; A61B 34/20; A61B 34/30; A61B 34/37; A61M 16/0488; A61M 2230/63
  See application file for complete search history.

(56) References Cited

U.S. PATENT DOCUMENTS

| | | | |
|---|---|---|---|
| 7,772,541 | B2 | 8/2010 | Froggatt et al. |
| 8,900,131 | B2 | 12/2014 | Chopra et al. |
| 9,452,276 | B2 | 9/2016 | Duindam et al. |
| 9,560,619 | B2 * | 1/2017 | Pijl ..................... H04W 64/00 |
| 2006/0013523 | A1 | 1/2006 | Childlers et al. |
| 2009/0118742 | A1 * | 5/2009 | Hartmann ............ A61B 34/20 901/14 |
| 2011/0160570 | A1 * | 6/2011 | Kariv ..................... A61B 6/12 600/424 |
| 2012/0203067 | A1 * | 8/2012 | Higgins ............ A61B 1/00133 600/117 |
| 2013/0258079 | A1 | 10/2013 | Rose et al. |
| 2013/0303892 | A1 | 11/2013 | Zhao et al. |
| 2014/0221921 | A1 | 8/2014 | Gilboa et al. |
| 2014/0343416 | A1 * | 11/2014 | Panescu ................. A61B 34/30 600/431 |
| 2015/0148690 | A1 | 5/2015 | Chopra et al. |
| 2015/0157468 | A1 | 6/2015 | Wakayama et al. |
| 2015/0327948 | A1 * | 11/2015 | Schoepp ................ A61B 5/061 600/424 |
| 2016/0158494 | A1 * | 6/2016 | Wenderow ............. A61B 90/98 604/95.01 |
| 2016/0228200 | A1 * | 8/2016 | Denissen ............... G01B 11/24 |
| 2016/0349044 | A1 * | 12/2016 | Marell .................... G01B 11/18 |
| 2017/0151026 | A1 | 6/2017 | Panescu et al. |
| 2018/0177383 | A1 * | 6/2018 | Noonan ................ A61B 34/74 |
| 2019/0192234 | A1 | 6/2019 | Gadda et al. |
| 2022/0143366 | A1 | 5/2022 | Adebar |

FOREIGN PATENT DOCUMENTS

| | | |
|---|---|---|
| CN | 106794044 A | 5/2017 |
| CN | 106794050 A | 5/2017 |
| KR | 101447931 B1 | 10/2014 |
| WO | WO-2013116140 A1 | 8/2013 |
| WO | WO-2014186715 A1 | 11/2014 |
| WO | WO-2016032902 A1 | 3/2016 |
| WO | WO-2016164311 A1 | 10/2016 |
| WO | WO-2017049163 A1 | 3/2017 |
| WO | WO-2018009841 A1 | 1/2018 |
| WO | WO-2018057633 A1 | 3/2018 |

OTHER PUBLICATIONS

International Preliminary Report on Patentability for Application No. PCT/US2018/046685, dated Feb. 27, 2020, 6 pages.
Office Action dated Jul. 27, 2021 for Chinese Application No. 201780048276.9 filed Aug. 14, 2018, 37 pages.
Extended European Search Report for Application No. EP18845627.1 dated Mar. 30, 2021, 10 pages.
International Search Report and Written Opinion for Application No. PCT/US2018/046685, dated Feb. 22, 2019, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP23189829.7, dated Nov. 8, 2023, 08 pages.

* cited by examiner

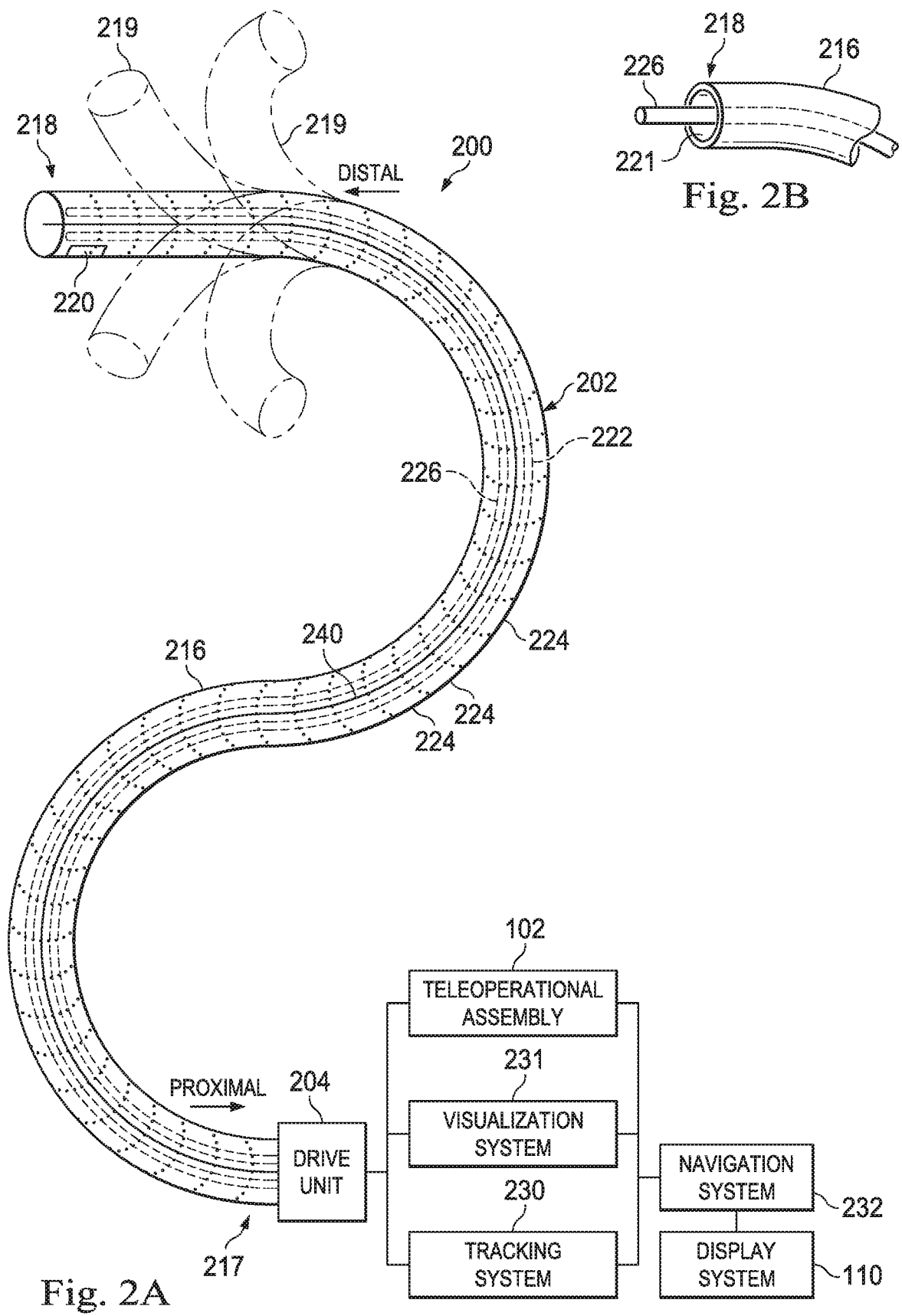

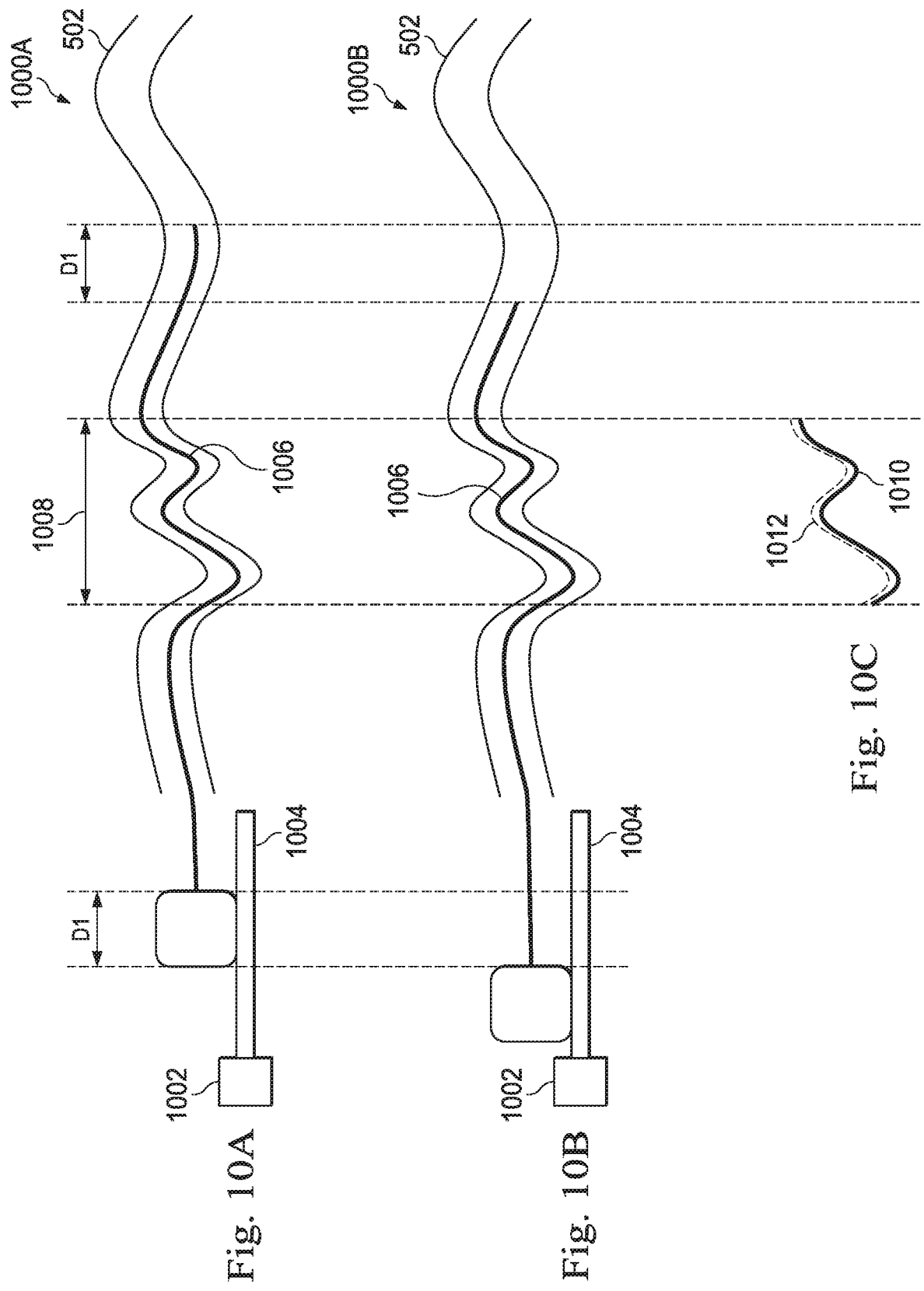

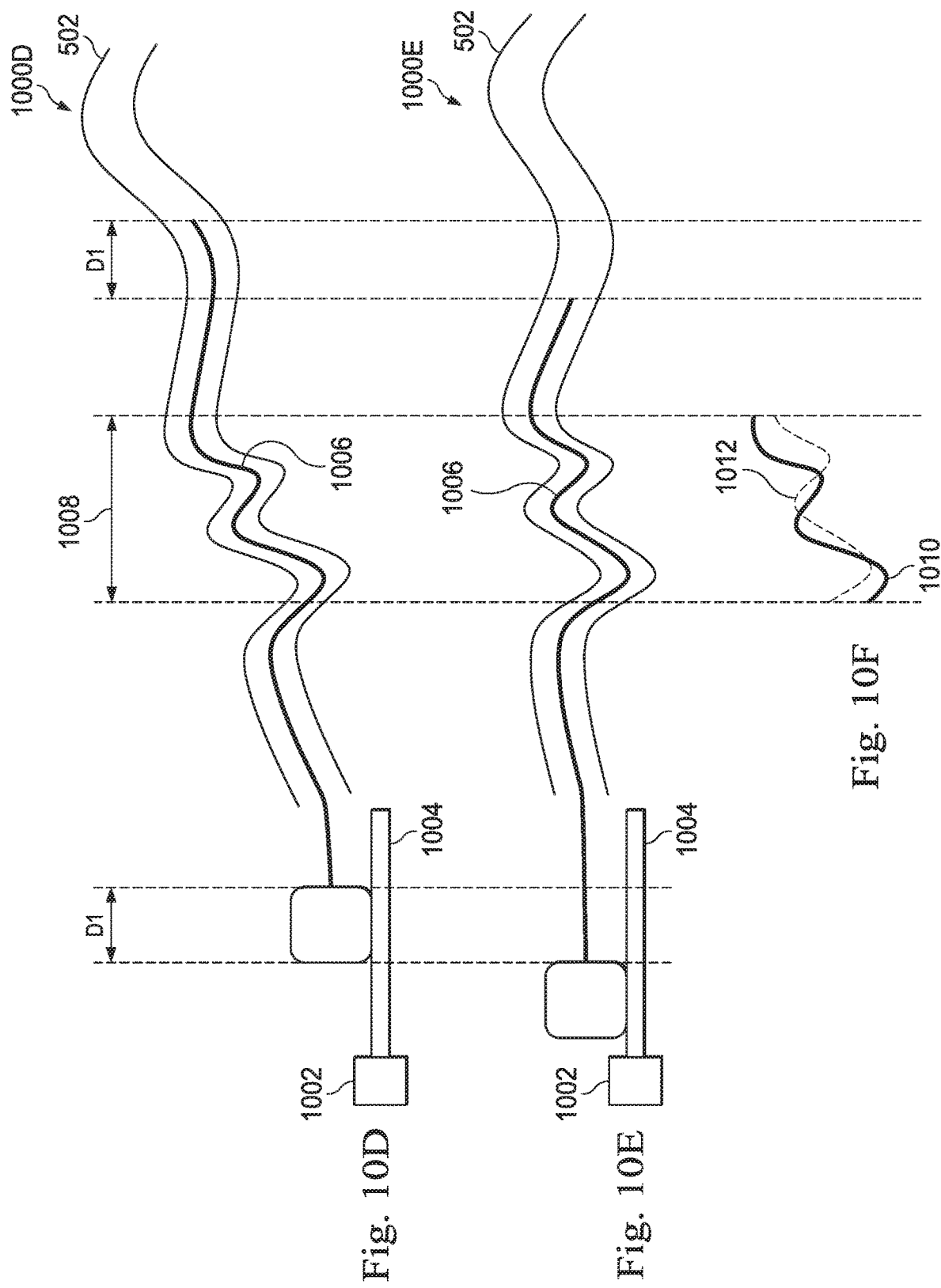

SYSTEMS AND METHODS FOR MONITORING PATIENT MOTION DURING A MEDICAL PROCEDURE

CROSS-REFERENCE TO RELATED APPLICATIONS

This patent application is the U.S. national phase of International Application No. PCT/US2018/046685, filed Aug. 14, 2018, which designated the U.S. and claims priority to and the benefit of the filing date of U.S. Provisional Patent Application No. 62/546,366, entitled "SYSTEMS AND METHODS FOR MONITORING PATIENT MOTION DURING A MEDICAL PROCEDURE," filed Aug. 16, 2017, all of which are hereby incorporated by reference in their entirety.

FIELD

The present disclosure is directed to systems and methods for monitoring the motion of a patient or of a medical system relative to the patient during a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Other minimally invasive techniques may include the user of relatively rigid devices manipulated within the patient anatomy. Control of such an elongate device by medical personnel involves the management of several degrees of freedom including at least the management of insertion and retraction of the elongate device as well as steering of the device. In addition, different modes of operation may also be supported.

During a medical procedure, the patient may move. In some instances, this may depend on the type of anesthesia the patient is placed under. For example, an involuntary bodily movement may occur, or the patient may be bumped or otherwise moved by a physician or another person present in the surgical environment. Additionally, the minimally invasive system may be moved relative to the patient. Such movements can cause complications during the minimally-invasive procedures, including image-guided medical procedures.

Accordingly, it would be advantageous to provide improved methods and systems for monitoring patient motion during a medical procedure.

SUMMARY

The embodiments of the invention are best summarized by the claims that follow the description.

Consistent with some embodiments, an exemplary method of controlling an elongate instrument during a medical procedure involving motion of the elongate instrument relative to a patient is provided. The method includes generating, by a control system, a first model of the elongate instrument, and generating, by the control system, a second model of the elongate instrument based on a reference pose of the elongate instrument. The method further includes comparing, by the control system, the first model with the second model and determining, by the control system, a state of a system configuration based on the comparison.

Consistent with some other embodiments, an exemplary medical system is provided. The medical system includes an elongate instrument having a sensor system, and a control system in communication with the sensor system to measure a pose of the elongate instrument. The control system is adapted to perform operations. Such operations may include generating a first model of the elongate instrument, and generating a second model of the elongate instrument based on a reference pose of the elongate instrument. The operations may further include comparing the first model with the second model, and determining a state of a system configuration based on the comparison.

Consistent with some other embodiments, an exemplary method is provided. The method includes generating, by a control system, a first model of an elongate instrument based on a measured state of the elongate instrument, and generating, by the control system, a second model of the elongate instrument based on a reference state of the elongate instrument and a user command. The method further includes comparing, by the control system, the first model with the second model, and determining, by the control system, a state of a system configuration based on the comparison.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2A is a simplified diagram of a medical instrument system according to some embodiments.

FIG. 2B is a simplified diagram of a medical instrument system with an extended medical tool according to some embodiments.

Figure 5A:
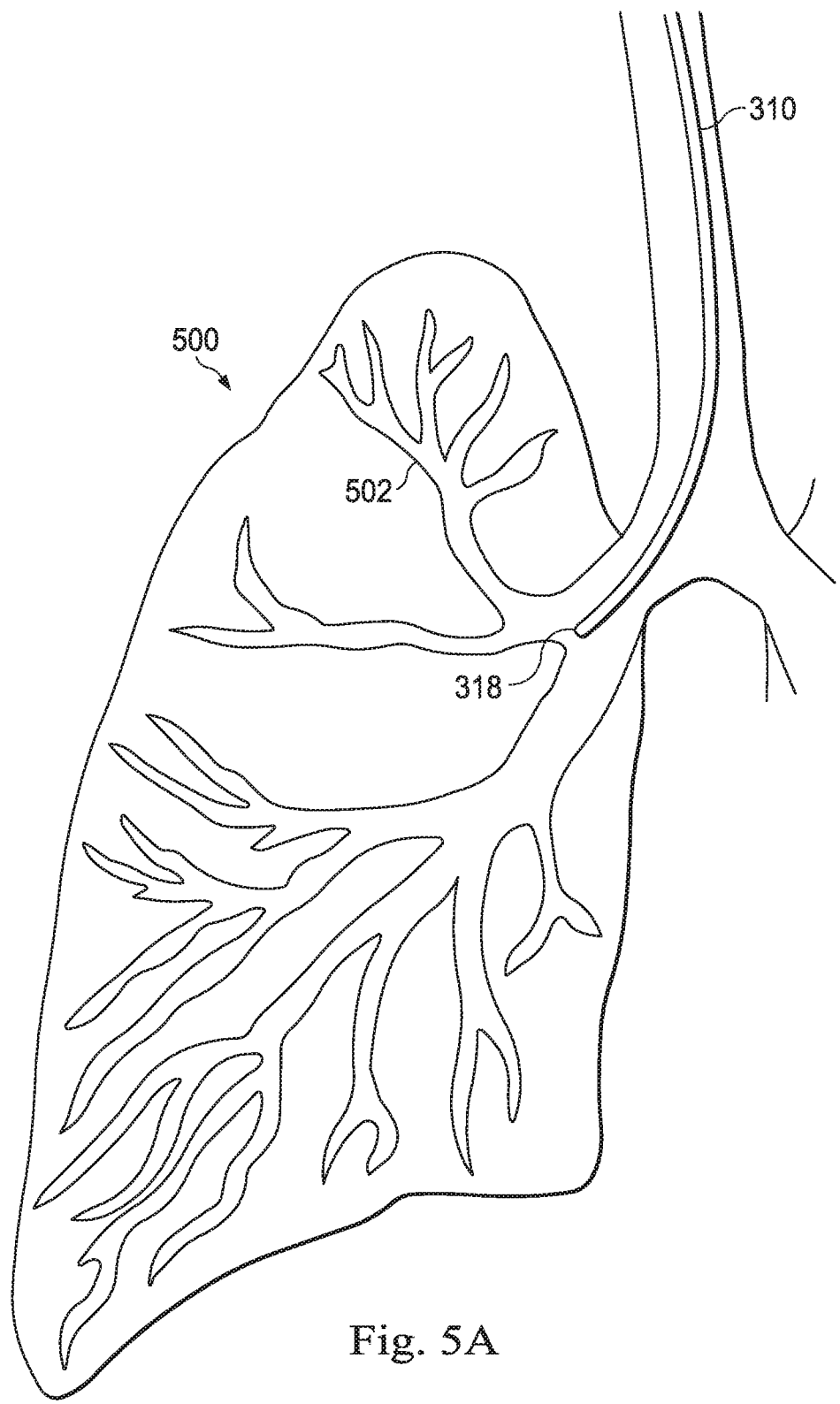
Figure 5B:
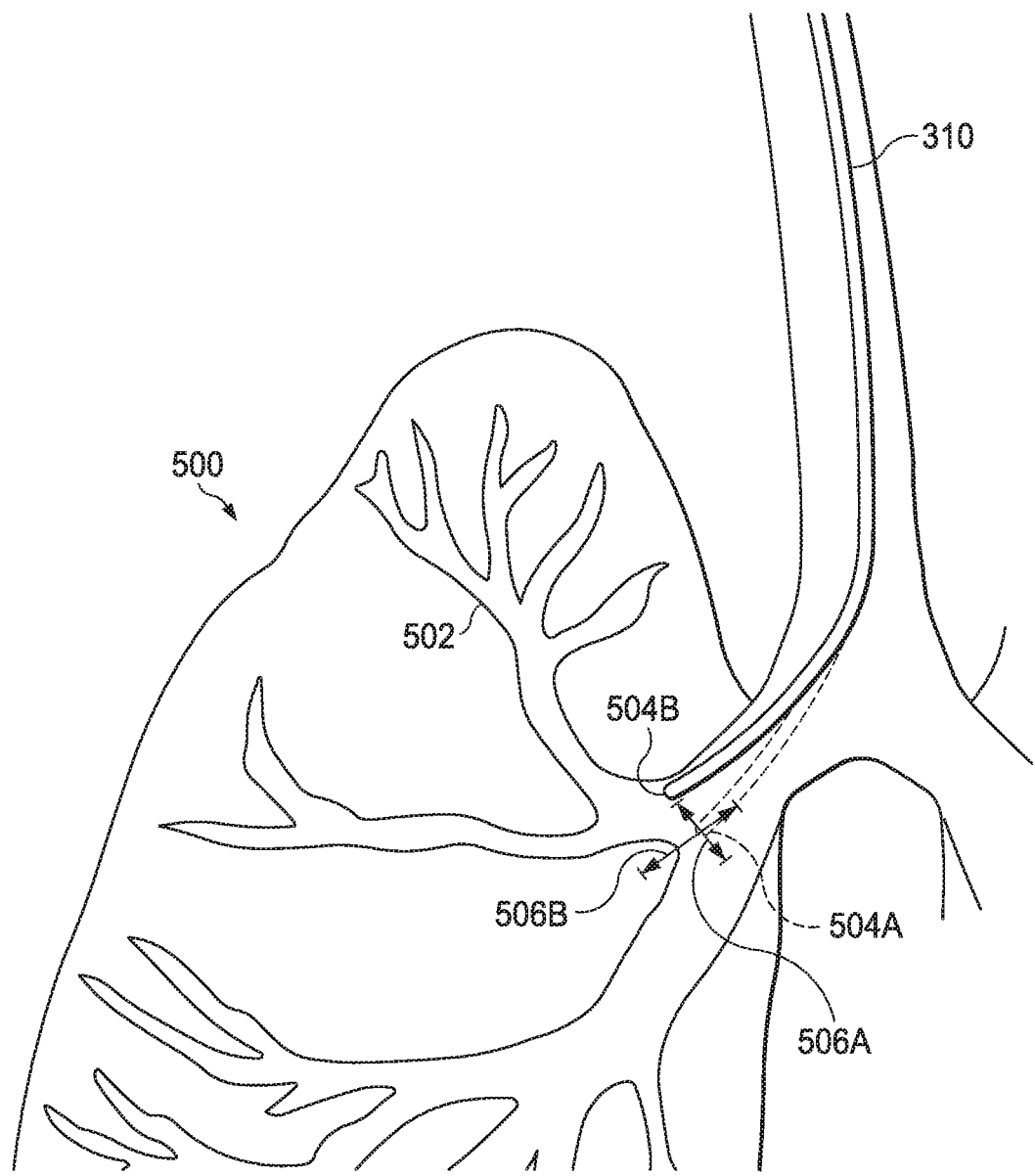
Figure 5C:
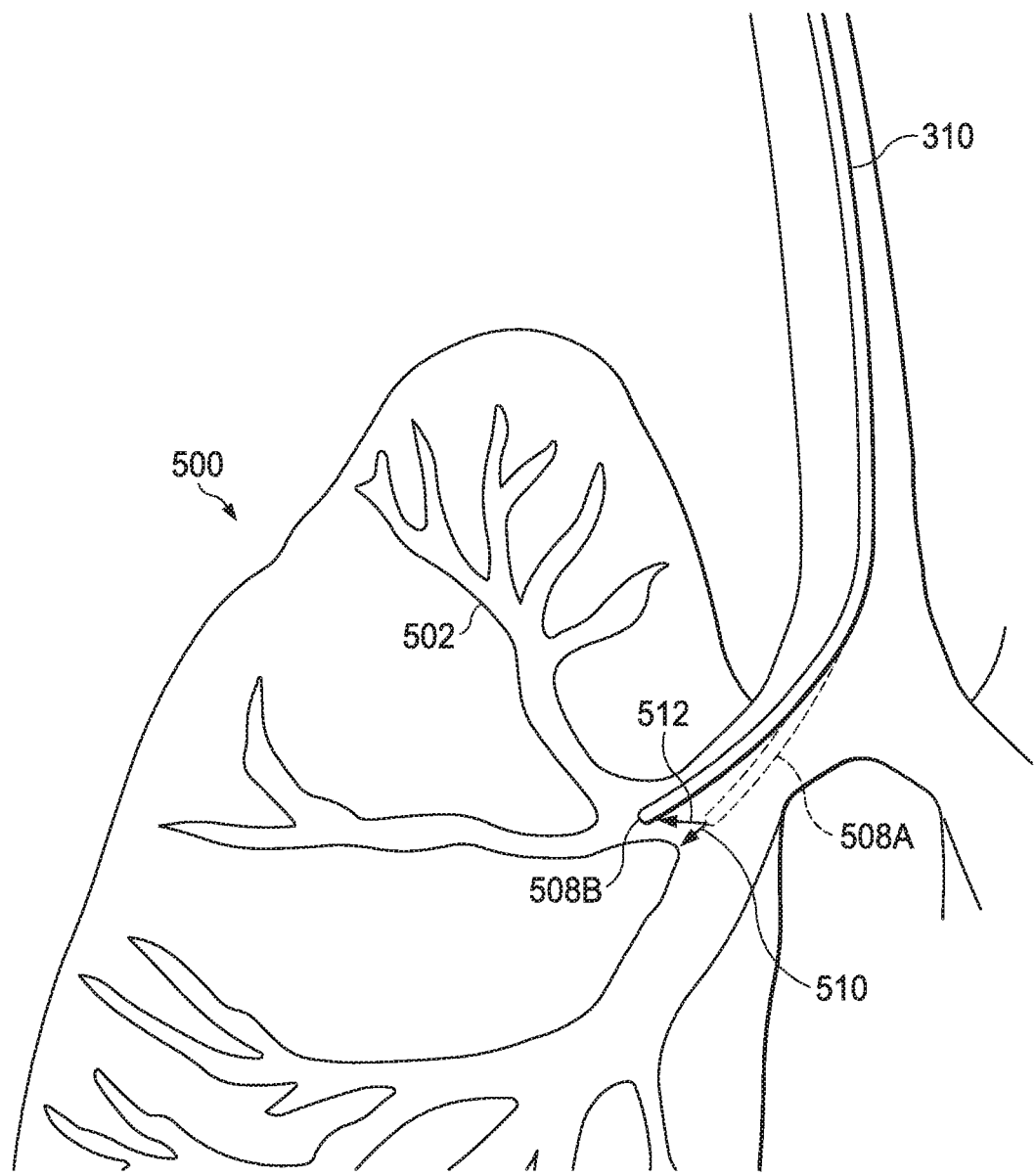

FIGS. 5A, 5B, and 5C illustrate the distal end of the medical instrument systems of FIGS. 2A-C, 3A, and 3B, during use within a human lung according to some embodiments.

Figure 6A:
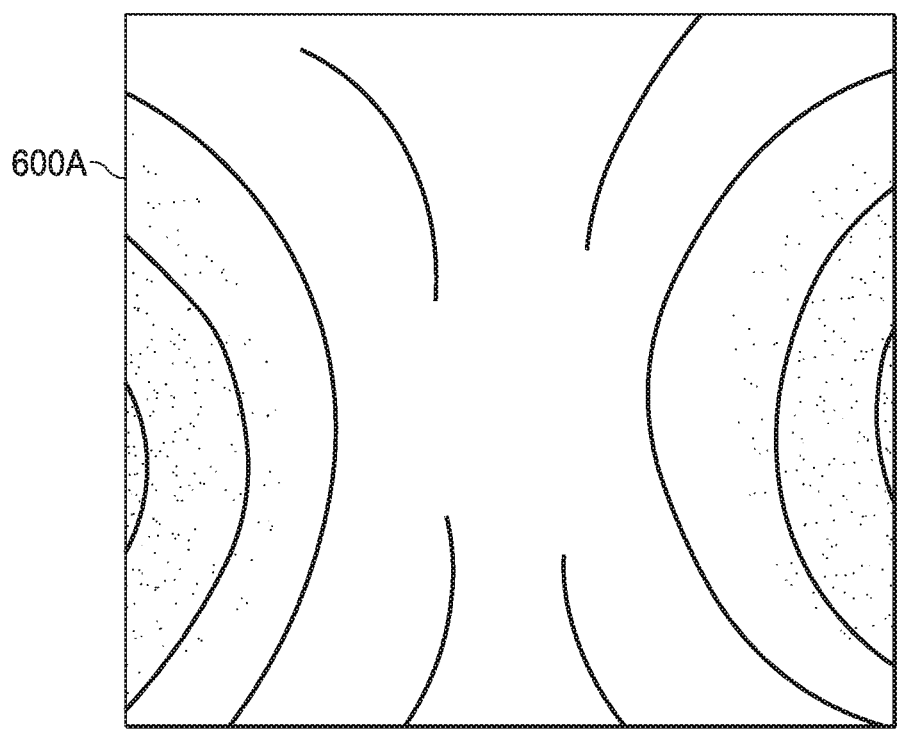
Figure 6B:
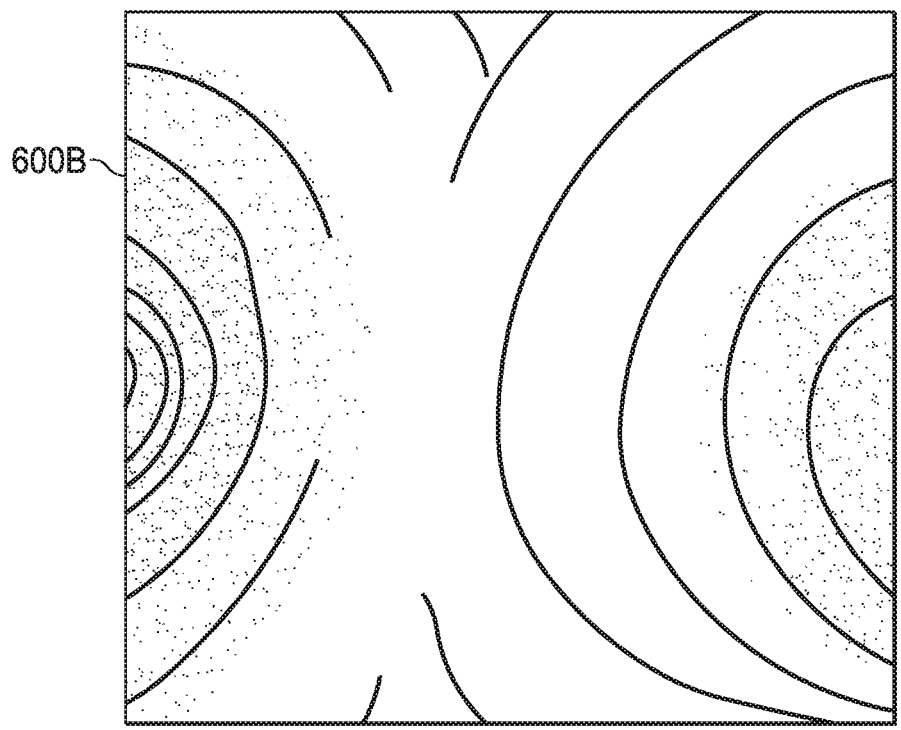

FIGS. 6A and 6B illustrate images that may be used in identifying patient motion according to some embodiments.

Figure 7:
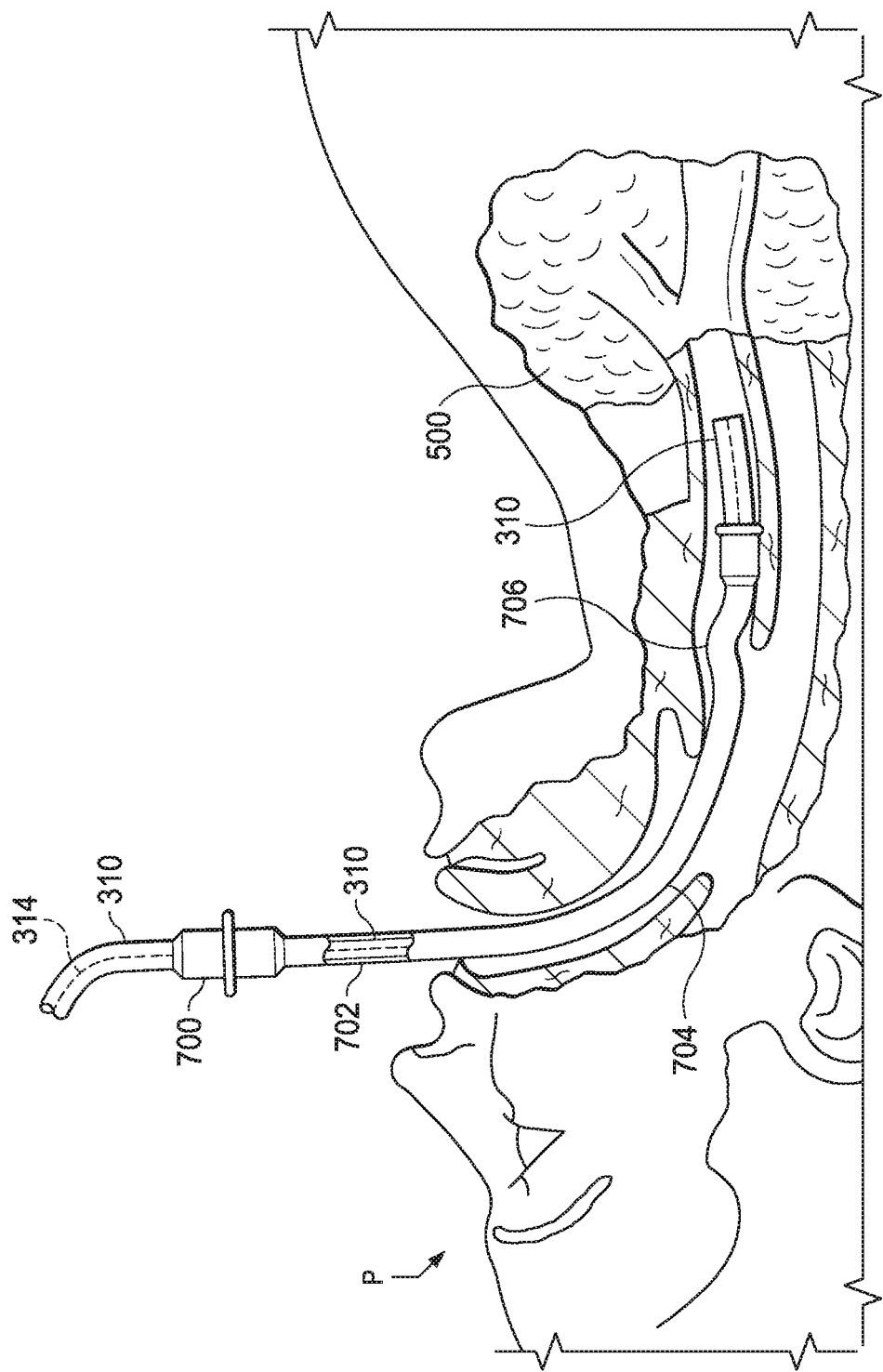

FIG. 7 depicts a simplified diagram of a side view of a patient having a endotracheal tube inserted to facilitate use to the medical instrument system according to some embodiments.

Figure 8:
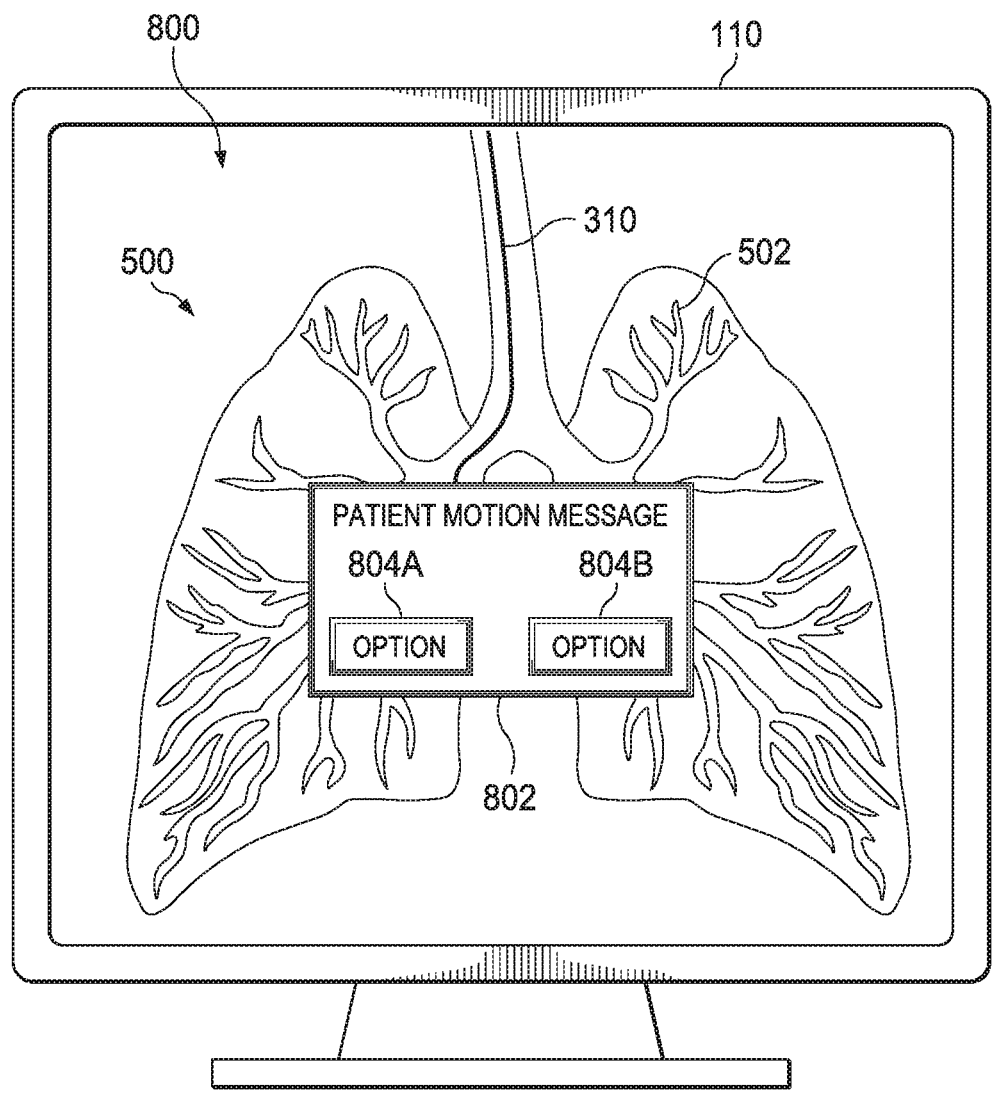

FIG. 8 depicts a user interface according to some embodiments.

Figure 9:
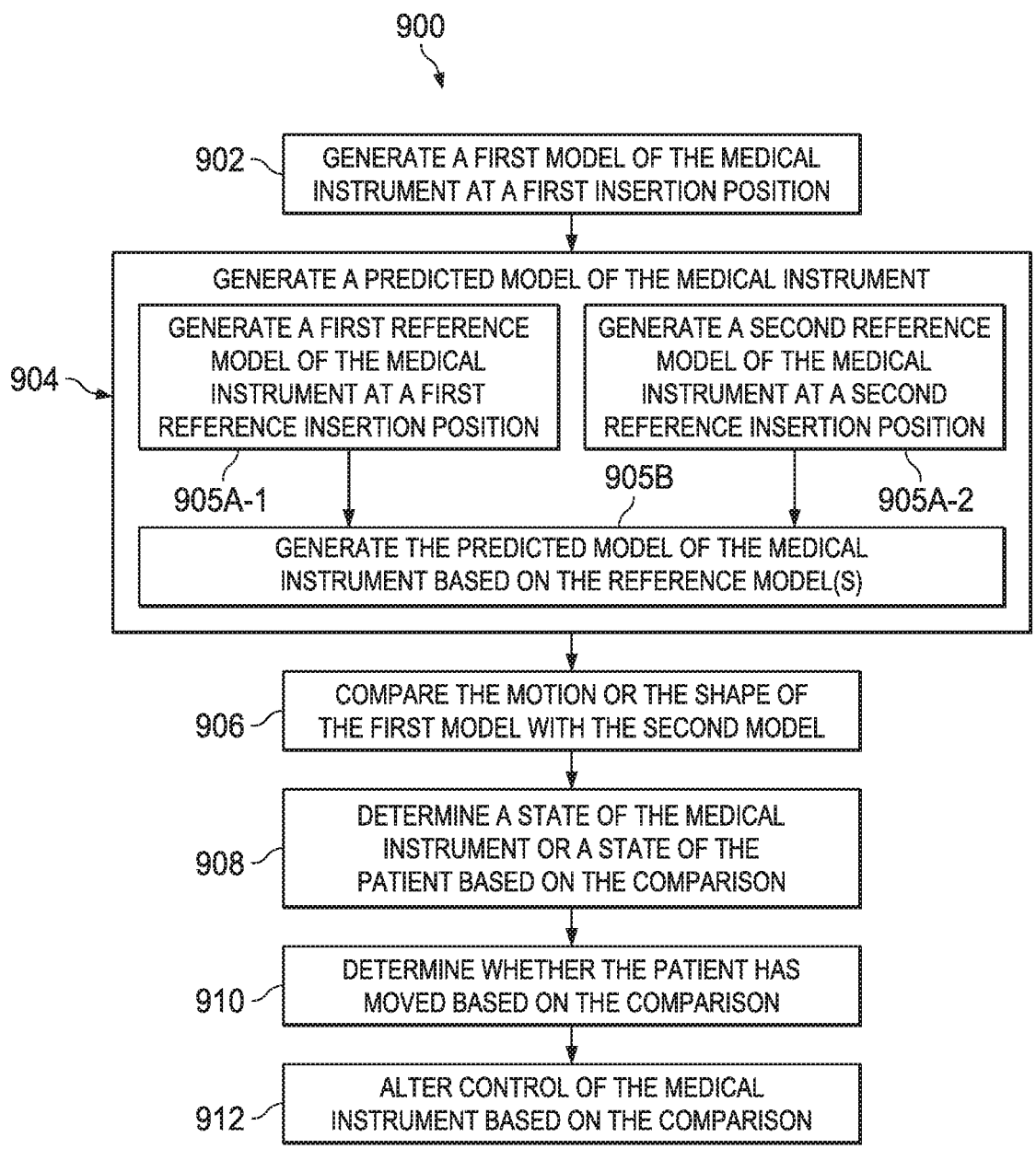

FIG. 9 is a flowchart of another method for monitoring patient movement during a medical procedure according to some embodiments.

FIG. 10A depicts a system configuration of a medical instrument associated with a measured model according to some embodiments.

FIG. 10B depicts another system configuration of the medical instrument of FIG. 10A associated with a reference model according to some embodiments.

FIG. 10C shows a portion of the measured model of FIG. 10A and a corresponding portion of a predicted model of the medical instrument, according to some embodiments.

FIG. 10D depicts another system configuration of a medical instrument associated with a measured model according to some embodiments.

FIG. 10E depicts another system configuration of the medical instrument of FIG. 10A associated with a reference model according to some embodiments.

FIG. 10F shows a portion of the measured model of FIG. 10D and a corresponding portion of a predicted model of the medical instrument, according to some embodiments.

Figure 11A:
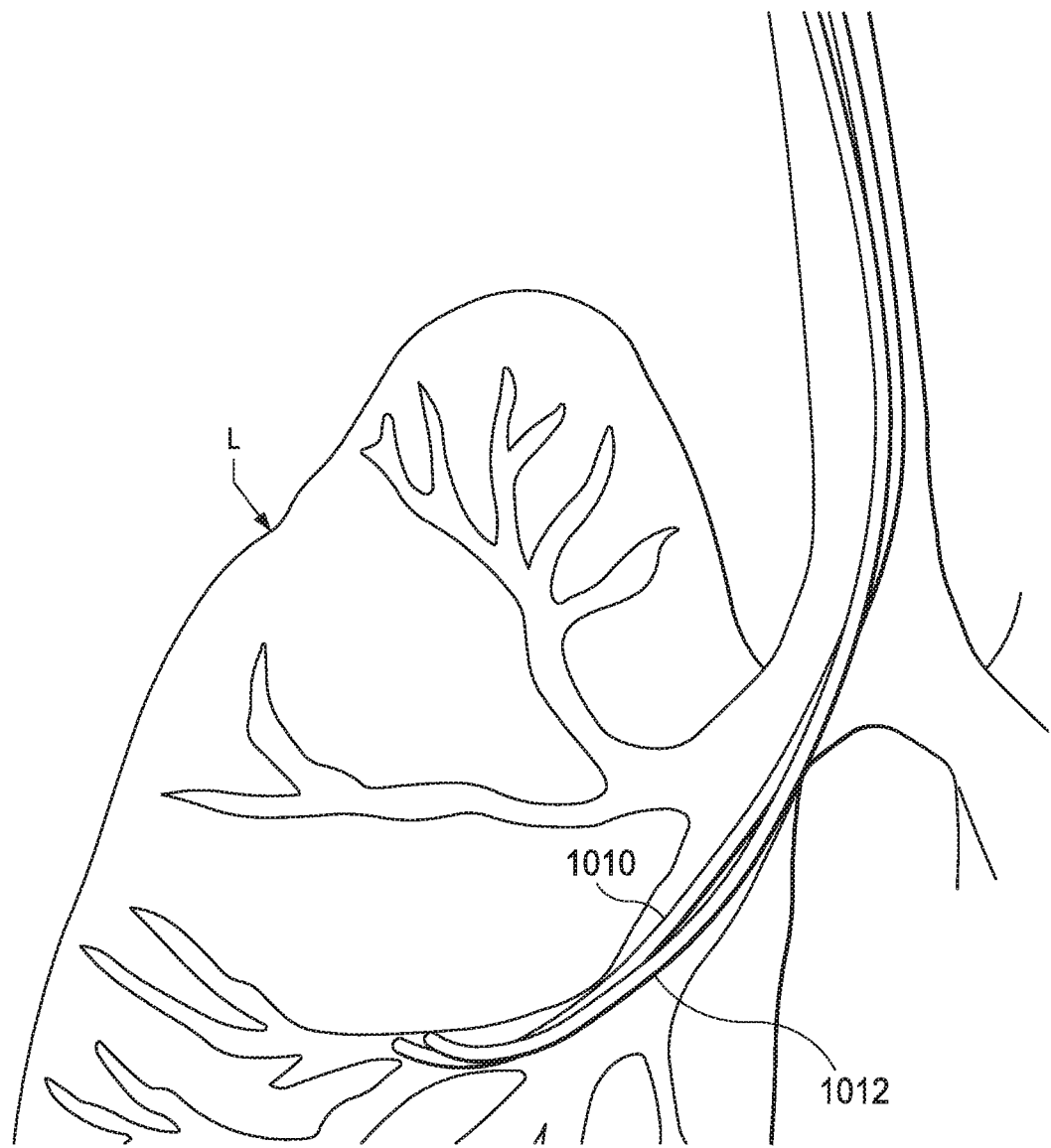
Figure 11B:
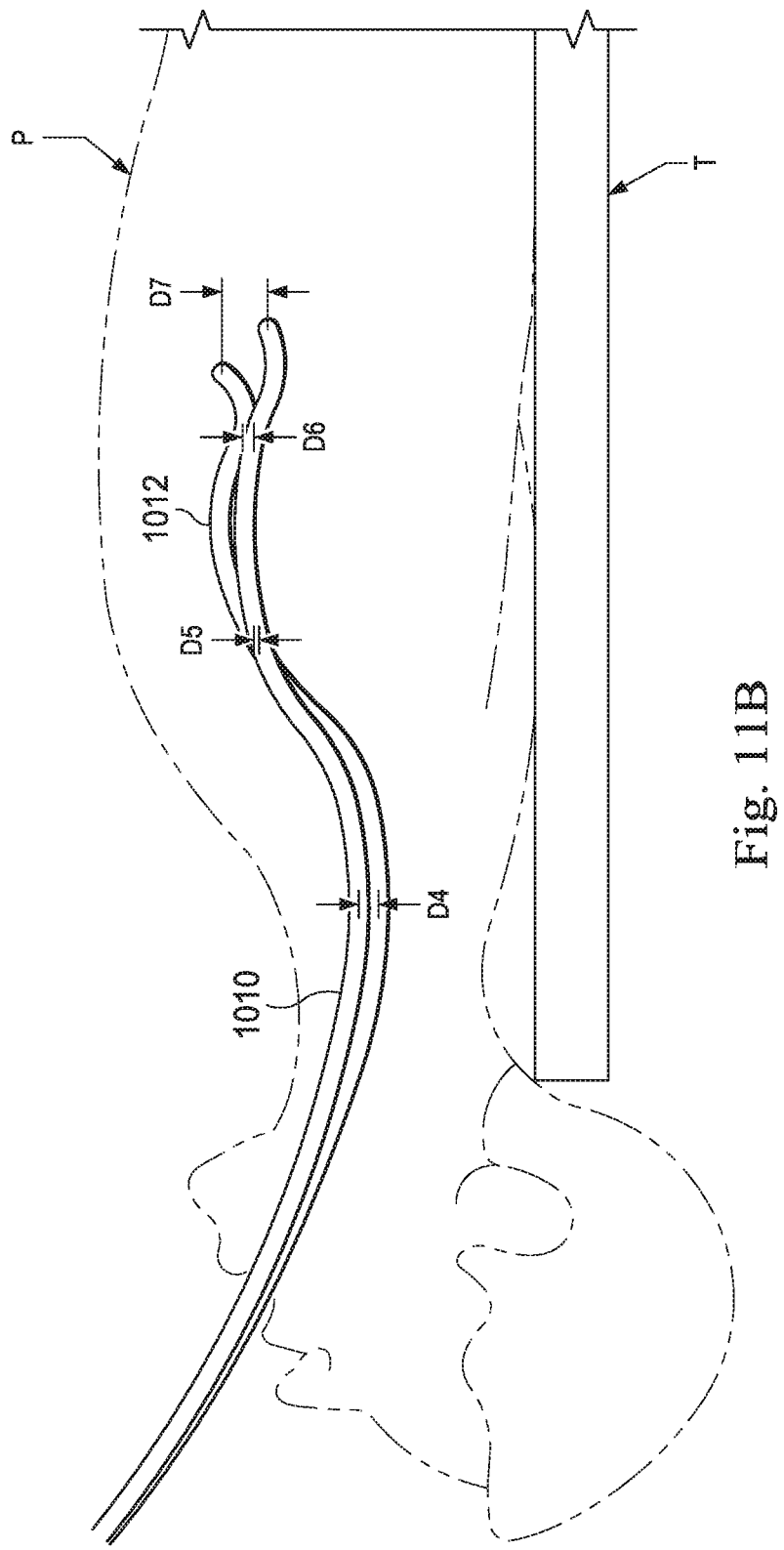

FIGS. 11A and 11B show representations of measured and predicted models that may be compared to determine patient motion according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their position, orientation, and/or pose in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

The disclosure is generally directed to methods and systems for monitoring the motion of a patient undergoing a medical procedure. In some approaches a dedicated device may be used to monitor a patient P. Embodiments of the present disclosure utilize information from assemblies and instruments that have a primary purpose other than monitoring patient motion. Accordingly, embodiments of the present disclosure may obviate the need of a dedicated patient motion monitoring device by enabling other systems and devices to secondarily provide patient motion monitoring means. The principles of the present disclosure may also be applied to dedicated devices to improve their accuracy and performance in monitoring patient motion. While some embodiments provided herein are discussed primarily with respect to medical procedures, any reference to medical or surgical instruments and medical or surgical methods is non-limiting. The systems, instruments, and methods described herein may be used for animals, human cadavers, animal cadavers, human or animal tissue removed from human or animal anatomy and not to be returned to such human or animal anatomy, non-surgical treatment, diagnosis, or cosmetic improvements. The systems, instruments, and methods described herein may also be used for industrial systems and general robotic or teleoperational systems, including those for manipulating or otherwise interacting with work pieces not comprising human or animal tissue.

Figure 1:
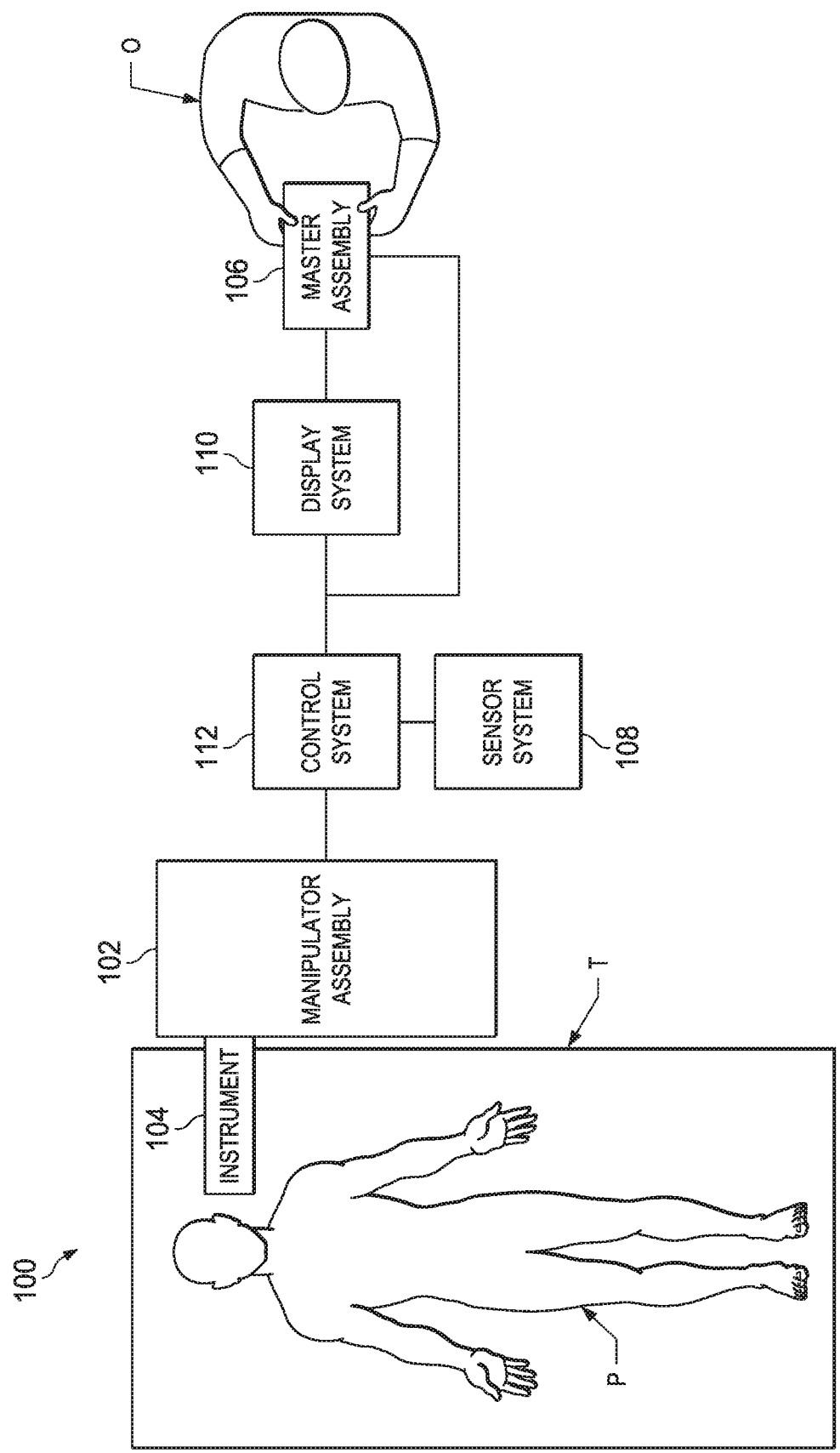
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. An input control device or master assembly 106 allows an operator O (e.g., a surgeon, a clinician, or a physician as illustrated in FIG. 1) to control teleoperational manipulator assembly 102 and, in some embodiments, to view the interventional site.

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that, when coupled to medical instrument 104, advance the medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to the medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104. The sensor system 108 may include a plurality of sensors disposed along a kinematic chain of the manipulator assembly 102, in some embodiments.

Teleoperated medical system 110 may also include a control system 112. Control system 112 includes at least one memory and at least one computer processor (not shown) for effecting control between medical instrument 104, master assembly 106, sensor system 108, and display system 110, and/or other components of the medical system 100. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used.

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensors, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

FIG. 2A is a simplified diagram of a medical instrument system 200 according to some embodiments, in some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

The medical instrument system 200 of FIGS. 2A and 2B includes elongate device 202 (also referred to as elongate instrument 202), such as a flexible catheter, coupled to a drive unit 204. The drive unit 204 may include a plurality of actuators that can be controlled to steer a distal portion of the elongate device. In some embodiments, the drive unit 204 may include capstans or rotating elements that can be rotated to steer at least a distal portion of the elongate device 202. Elongate device 202 includes a flexible body 216 having proximal end 217 and distal end 218.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230 may be included as a subsystem of the control system 112. Thus, tracking system 230 may optionally be implemented as hardware, firmware, software or a combination thereof, which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). The optical fiber of shape sensor 222 forms a fiber optic bend sensor for determining the shape of flexible body 216. In one alternative, multiple optical fiber cores including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by, reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating physiological motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The drive unit 204 may include sensors or encoders that produce linear or rotational position data, force data characterizing a force applied by the drive unit 204 on a particular cable, and/or tension data characterizing a tension on a particular cable. Additionally, some embodiments of the drive unit 204 may include a sled or carriage that can be controlled to move the proximal end 217 of the flexible body 216, and thereby the distal end 218, along an insertion axis. The position of the carriage along the insertion axis may be monitored by a sensor or encoders. As noted herein, the sensors or encoders that provide position data may also provide velocity data and acceleration data that characterize movement of a medical instrument system like the medical instrument system 200, for example.

Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use by the physician O in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

Figure 2C:
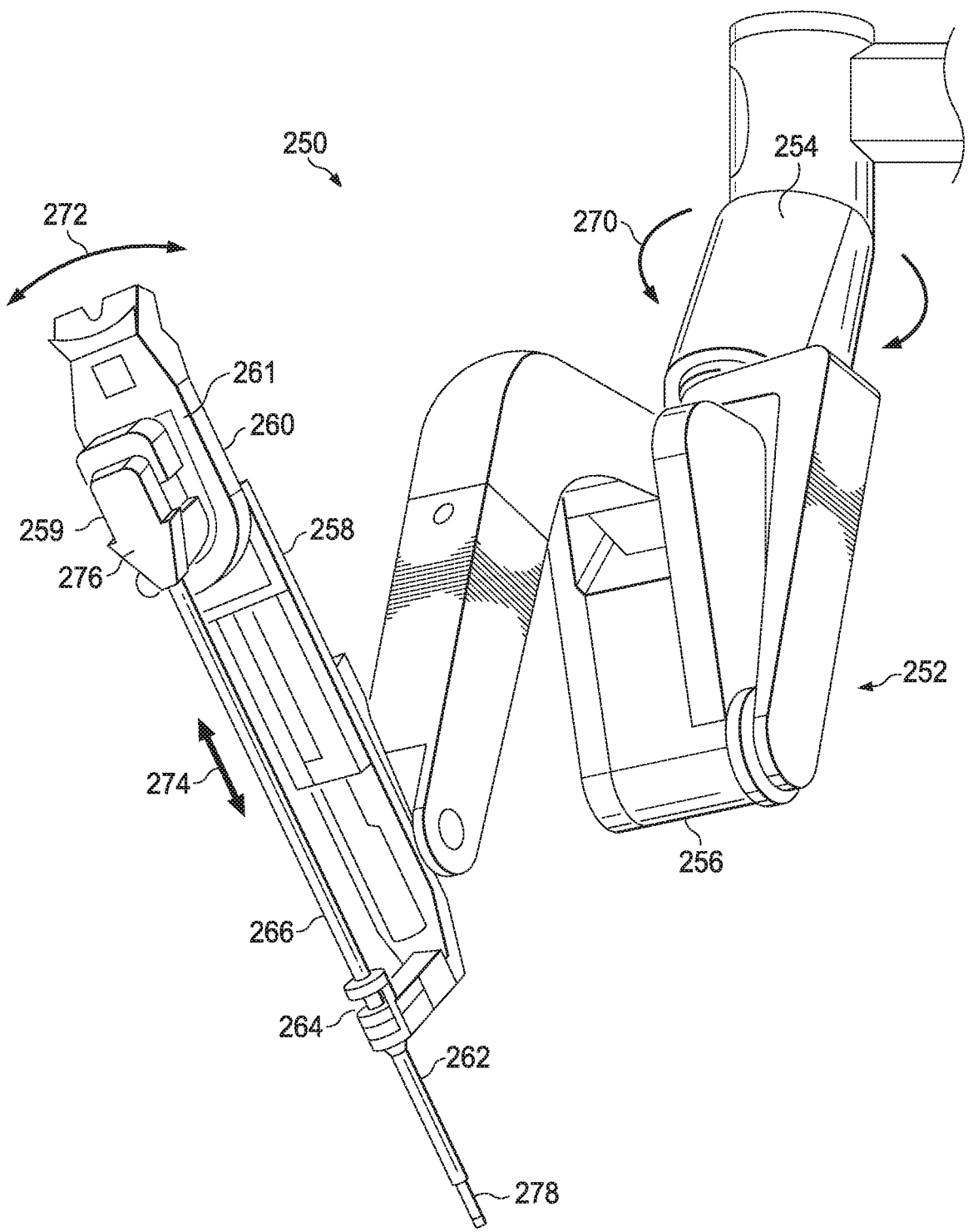
FIG. 2C is a diagram of a medical instrument system with a kinematic chain according to some embodiments.

FIG. 2C illustrates a medical instrument system 250, which may be used as the medical instrument system 104 in a medical procedure performed with teleoperated medical system 100. FIG. 2C is a perspective view of a manipulator 252 of a control arm that may be mounted to or incorporated into the manipulator assembly 102 of FIG. 1. The medical instrument system 250 includes a kinematic chain made up of a plurality of joints. At least some of the joints in the kinematic chain include joint sensors or encoders that can communicate with the control system 112 of FIG. 1 to provide joint sensor data to facilitate monitoring and control of the medical instrument system 250. The joint sensor data may include position data such that the control system 112 can generate a model of the medical instrument system 250, such that when a back end position and orientation of the manipulator 252 is known, a distal end position and orientation of each component along the kinematic chain of the medical instrument system 250.

The manipulator 252 includes a yaw servo joint 254, a pitch servo joint 256, and an insertion and withdrawal ("I/O") actuator 258. A surgical instrument 259 is shown mounted at an instrument spar 260 including a mounting carriage 261. Yaw servo joint 254 provides yaw motion 270, pitch joint 256 provides pitch motion 272, and I/O actuator 258 provides insertion and withdrawal motion 274 through the remote center. The manipulator 252 may include an encoder to track position, velocity, and/or acceleration associated with servo positions along the insertion axis of the I/O actuator 258 and other encoders to track position and velocity of yaw servo joint 254 and pitch servo joint 256.

In some examples, medical instrument system 200 or the medical instrument system 250 may be teleoperated within the context of the medical system 100 of FIG. 1 as the manipulator assembly 102 or a component thereof. In some embodiments, teleoperational manipulator assembly 102 of FIG. 1 may be replaced by direct operator control. In some examples, the direct operator control may include various handles and operator interfaces for hand-held operation of the instrument.

Figure 3A:
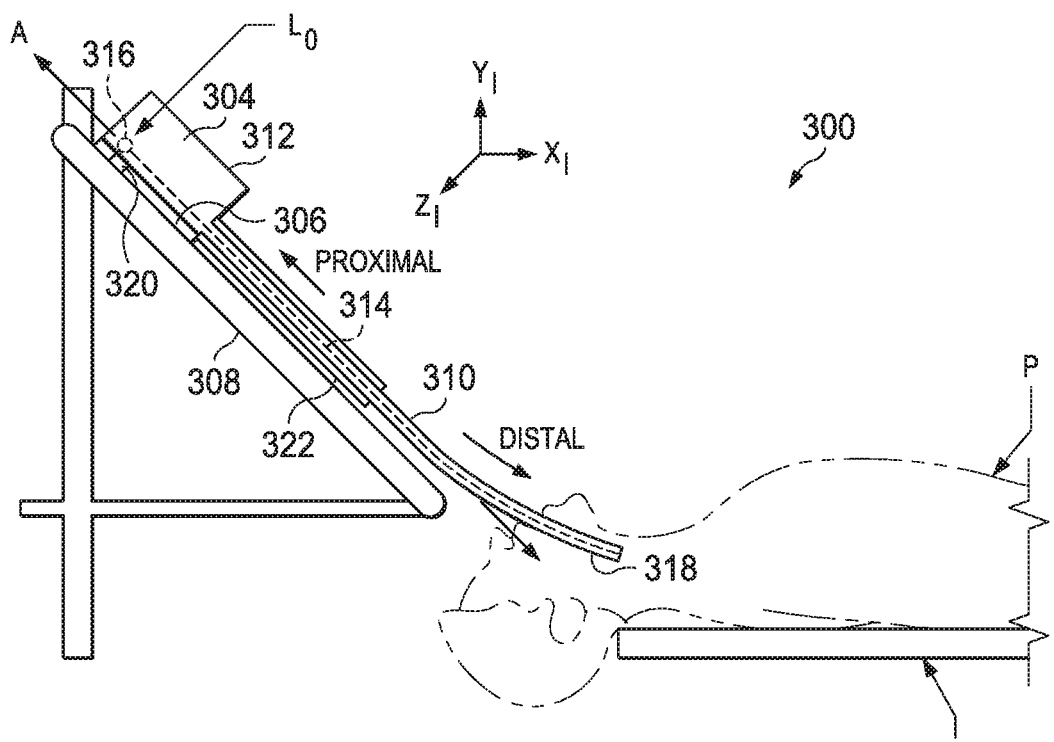
FIGS. 3A and 3B are simplified diagrams of side views of a patient in patient coordinate space including a medical instrument mounted on an insertion assembly according to some embodiments.
Figure 3B:
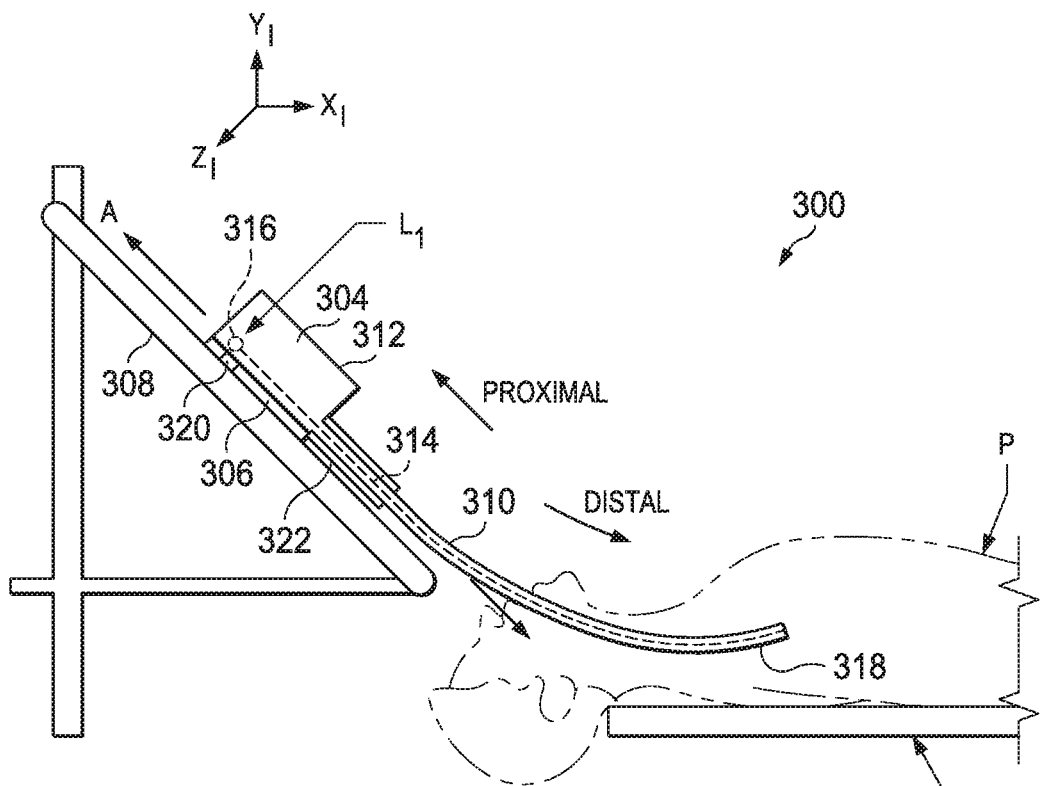

FIGS. 3A and 3B are simplified diagrams of side views of a patient coordinate space including a medical instrument mounted on an insertion assembly according to some embodiments. As shown in FIGS. 3A and 3B, a surgical environment 300 includes the patient P is positioned on the operating table T. Within surgical environment 300, a medical instrument 304 is coupled to an instrument carriage 306. The medical instrument 304 may be provided by the medical instrument system 200 of FIGS. 2A and 2B. In some embodiments, medical instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to medical instrument 304 to control insertion motion (i.e., motion along the A axis) and, optionally, motion of a distal end 318 of an elongate device 310 in multiple directions including yaw, pitch, and roll. The elongate device 310 may be a flexible, steerable catheter. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Medical instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

FIGS. 3A and 3B also depict an anti-buckling guide 322, which is an extendible mechanism, such as a lattice or other deployable structure, that supports the proximal end of the elongate device 310 during insertion and retraction. Additional details of exemplary extendible mechanisms are included in the disclosure of PCT/US17/41160 filed Jul. 7, 2017 titled "Guide Apparatus for Delivery of an Elongate Device and Methods of Use," which is incorporated herein in its entirety.

Figure 4:
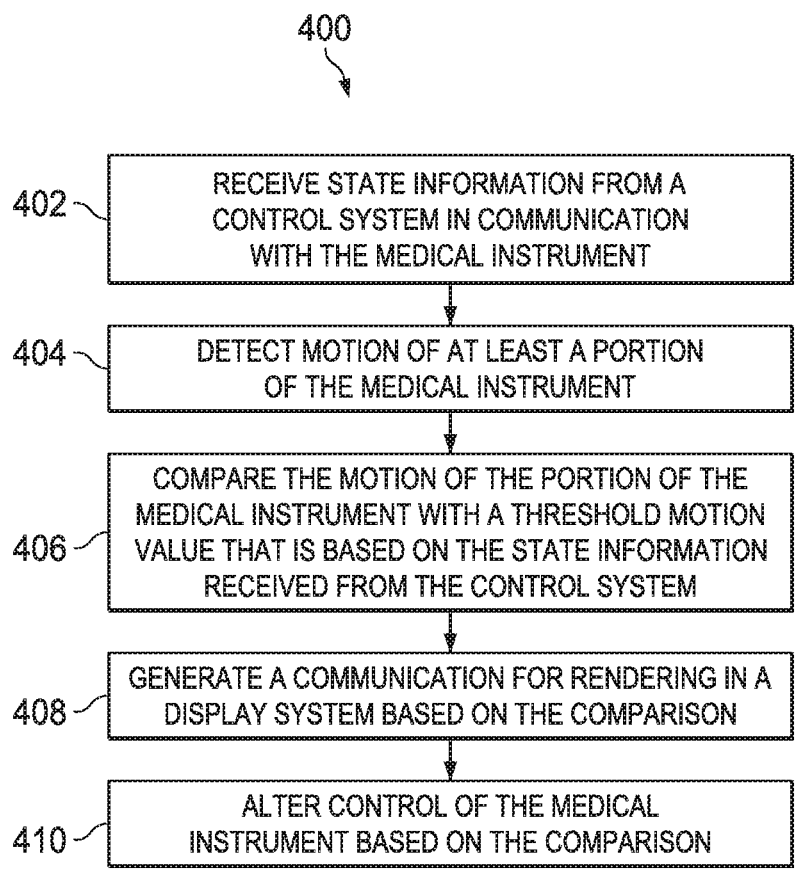
FIG. 4 is a flowchart of a method for monitoring patient movement during a medical procedure according to some embodiments.

FIG. 4 is a flowchart of a method 400 of monitoring patient motion during a medical procedure to detect motion of the patient undergoing the procedure. The method 400 may utilize a medical instrument having a primary purpose other than patient motion monitoring. As illustrated in FIG. 4, the method 400 includes several enumerated steps or operations, which may be performed in the illustrated sequence. Embodiments of the method 400 may include additional or alternative operations before, after, in between, or as part of the enumerated operations. Some embodiments of the method 400 may omit one or more of the enumerated operations. Furthermore, embodiments of the method 400 may include executable instructions stored on a computer-readable medium and executed by a processor, such as a processor of the control system 112 of FIG. 1, to perform the operations of method 400.

Accordingly, an embodiment of the method 400 may begin at operation 402 in which state information may be received from a control system in communication with the medical instrument. At operation 404, the control system may detect motion of at least a portion of the medical instrument. The control system may compare the motion of the portion of the medical instrument with a threshold motion value that is based on the state information received from the control system, at operation 406 to determine a state of the medical instrument or the patient. This may include determining patient motion. At operation 408, the control system may generate a communication for rendering in a display system based on the comparison of the motion with the threshold motion value and determination of patient motion. And at operation 410, the control system may alter control of the medical instrument based on the comparison. For example, the control system may alter control of the medical instrument by putting the medical instrument in a safe state or safe mode. This safe state may include removing power from a drive unit, like the drive unit 204 of FIG. 2A, so that the medical instrument becomes compliant or limp. In some embodiments, the safe state may alter control of additional medical instrument or of instrument introduce via the medical instrument, such as an ablation probe or other energized instrument. In the safe state, the control system may disconnect or power down an energy supply provided to the energized instrument.

To better explain embodiments of the method 400, reference is made herein to additional FIGS. 5A-C and 6A-B, which relate to the positioning of the elongate device 310 of FIGS. 3A and 3B through anatomic passageways 502 of the lungs 500 of the patient P of FIGS. 1 and 3. These passageways 502 include the trachea and the bronchial airways. As shown in FIGS. 3A and 3B, as the carriage 306 moves along the insertion stage 308, the elongate device 310 is advanced within the anatomic passageways 502 of the lungs 500. To navigate the elongate device 310 within the lungs 500, the physician O may steer the distal end 318 of the elongate device 310 while directing the movement of the carriage 306 along the insertion axis A. In navigating through the anatomic passageways 502 (i.e., in a drive state or drive mode), the elongate device 310 assumes a shape that may be measured by the shape sensor 314 extending within the elongate device 310. The control system 112 may also interrogate the shape sensor 314 and/or additional sensors that may provide shape and/or positional information (such as electromagnetic systems and/or joint sensors) when the elongate device 310 is in a parked state or parked mode in which no movement commands are received via the master assembly 106 from the physician O. At operation 402, the state of the medical system 100 may be received by, the control system 112 from state information indicating which of several possible states is currently implemented. In addition to the parked state and the drive state, the medical system 100 may have a treatment state in which a medical treatment is being applied to the patient anatomy proximate the distal end 318 of the elongate device 310. For example, the medical treatment may be the insertion of a biopsy needle, an ablation process, a cauterization process, an imaging process, an injection or drug delivery process, or any other medical treatment.

As described herein, in order to navigate to a desired location, the teleoperated medical system 100 may provide real-time imaging to the physician O. The real-time images may be captured images. In some embodiments, an image capture device is positioned at the distal end 318 of the elongate device 310. The real-time images may be simulated or virtual images rendered based on a computer model derived from preoperative images or intraoperative images. The virtual images may depict the elongate device 310 in images that show an external perspective of the patient P. Additionally, the virtual images may depict a representation of the interior surfaces of the passageways 502 of the lung 500 from a perspective determined by the position and orientation of the distal and 318 of the elongate device 310. Such imaging is discussed in more detail in connection with FIGS. 6A and 6B, described further below.

At operation 404, the control system 112 may detect motion of at least a portion of the elongate device 310. Motion may be detected by monitoring for a change in the position of the elongate device 310 over time. For example, the position of the elongate device 310 may be sampled 10 times per second, 100 times per second, or at another suitable frequency. As shown in FIG. 5B, the distal tip 318 of the elongate device 310 has moved from a first position 504A to a second position 504B. This motion may be quantified using information from the fiber optic shape sensor 314, an electromagnetic position sensor, or by comparison of optical images obtained within the anatomical passageways 502. The control system 112 may compare the movement between the first and second positions 504 with a threshold movement value. The threshold movement value may be implemented by the control system 112 to prevent false identification of movement of the distal end 318 as patient movement. For example, due to temperature fluctuations or other minor changes, a change in the indicated position of the distal tip 318, or another portion of the elongate device 310, may be registered without any significant positional change or movement taking place.

As illustrated in FIG. 5B, the threshold movement value may be determined relative to the direction of movement. As shown, lateral movement of the distal tip 318 may have a threshold movement value 506A, while the insertion/withdrawal (I/O) movement may have a threshold movement value 506B. As illustrated, the lateral threshold movement value 506A may be less than the I/O threshold movement value 506B, in some embodiments. Additionally, the magnitude of the threshold movement values 506 may be dependent upon the state of the medical system 100. For example, when the state information received at operation 402 indicates that the medical system 100 (or the manipulator assembly 102 thereof) is in a parked state, the magnitude of the threshold movement values 506 may be smaller than when the state information indicates a drive state. Furthermore, the threshold movement value may be realized as a shape in three-dimensions around the distal tip 318, in some embodiments. Thus, a given movement of the distal tip 318 in Cartesian X, Y, and Z coordinates that moves beyond that three-dimensional threshold may be regarded by the control system 112 as indicative of patient motion. The shape may be circular, ovoid, rectangular, symmetric, asymmetric, or otherwise shaped. The three-dimensional threshold shape may be defined in part by the threshold movement values 506 and be a function thereof. In some embodiments, the frequency of detected movement and threshold movement may be quantified and compared alternatively or in addition to magnitude of detected and threshold movements to determine patient motion.

In general, actual movement of the elongate device 310 may occur when the medical system 100 is in the parked state due to cyclical physiological motion, such as respiratory motion in the lung 500. In other embodiments, cardiac motions may be detected from shape/position information obtained from the elongate device 310. Such expected natural motions may be considered by the control system 112 when identifying patient motion. In order to avoid incorrectly triggering the control system 112 to identify motion of the patient P due to expected physiological motion, the threshold movement values 506 associated with the parked state may be sufficient to account for such physiological motion. The shape/position information obtained from the elongate device 310 during the parked state may be used to identify and quantify, physiological motion such as from heartbeat or respiration. For example, shape/position information may be collected over a period of time and when identified as cyclical or periodic, can be considered physiological motion. The magnitude of the periodic motion can be used to help determine a value for threshold movement values used to establish patient motion. In additional embodiments, because the effect of physiological motion may depend upon the position of the elongate device 310, the magnitude of the threshold movement values 506 may be based on an insertion depth or a three-dimensional position of the distal tip 318. For example, because the main bronchii of the lungs 500 may move less than the bottom lobe of the lungs 500 during normal respiration, the threshold movement values may be lower when the portion of the elongate device 310 being monitored is positioned within the main bronchii than when it is positioned more deeply in the lungs 500. In alternative embodiments, physiological motion can be detected using separate sensors or equipment such as a respiratory monitor, monitoring an artificial respirator, monitoring an electro-cardiogram of the patient, monitoring thoracic movement of the patient using a movement pad, and/or the like.

As shown in FIG. 5B, the distal tip 318 has moved a distance greater than the lateral threshold movement value 506A. Consequently, when the control system 112 compares the movement of the distal tip 318 with the lateral threshold movement value 506A at operation 406, the control system 112 may detect the movement as indicative of significant movement of the patient P.

Referring now to FIG. 5C, patient motion may be detected during a drive state as well. As noted above, the threshold movement values 506 may be different when the medical system 100 is in a drive state than when the medical system 100 is in a parked state. Additionally, when the medical system 100 is in a parked state as indicated by state information received at operation 402, the control system 112 may receive and analyze movement commands from the physician O as provided via the master assembly 106. For example, prior to receipt of a movement command, the distal tip 318 of the elongate device 310 may be in a first position 508A. A received movement command may be represented by the commanded motion vector 510. In other words, the movement command received from the physician O is intended to and should direct the distal tip 318 (and the trailing portions of the elongate device 310) to move as indicated by the vector 510, e.g. toward the wall alt the first branch point in the bronchus.

Instead, the distal tip 318 moves to a second position 508B, as shown in FIG. 5C. This movement may be calculated by the control system 112 as the actual motion vector 512, which is different than the commanded motion vector 510. Because the state information indicates that the medical system 100 is in a drive state, the control system 112 may compare the commanded motion vector 510 with the actual motion vector 512 and determine a difference therebetween. When the difference between the commanded motion vector 510 and the actual motion vector 512 exceeds a threshold motion value, the control system 112 may determine that some motion of patient P has occurred. In some embodiments, actuator current or torque may be measured and compared to the actual motion vector 512. The comparison can be evaluated against a threshold actuator value to determine patient motion. For example, actuators may apply an amount of torque to hold or move the elongate device 310 at or to a desired position. If the elongate device 310 made contact with tissue during patient motion, the amount of torque required for the desired motion would be increased above the threshold actuator value indicating patient movement.

Referring now to FIGS. 6A and 6B, shown therein are images that may be used by the control system 112 to determine a motion of the distal tip 318 of the elongate device 310. FIG. 6A includes an image 600A that represents a virtual view from the distal tip 318. This virtual view is an interior view of a model of the lungs 500, such as a surface model derived from preoperative or intraoperative medical images, such as a CT scan. FIG. 6B includes an image 600B that represents an actual view obtained by an image capture device positioned at the distal tip 318 of the elongate device 310 positioned within lungs 500. The control system 112 may select to the virtual view of image 600A based on the state indicated by the received state information, in some embodiments. For example, when the medical system 100 is in a parked state, a position and orientation of the distal tip 318 of the elongate device 310 may be used to generate a virtual view of the three-dimensional surface model of the lungs from the perspective indicated by the position and orientation. When the medical system 100 is in a drive state, the control system 112 may generate and use a predicted perspective of the distal tip 318, so that the actual image 600B may be compared with the portion of the surface model that should be in view at a given time based on the commanded motion of the distal tip 318. The control system 112 may utilize image processing techniques to compare the virtual view of the image 600A with the actual view of the image 600B. Depending on the relationship between the images 600, the control system 112 may be able to estimate a difference in the perspectives therebetween.

In some embodiments, the control system 112 may search the model to find an image best corresponding to the actual image 600B and then calculate a difference in position and orientation therebetween. The position of the expected image 600A and the position of the searched-for image identified in the model corresponding best to the actual image 600B may be calculated by the control system 112. Additionally, the control system 112 may compare the actual image 600B with the virtual image 600A to determine a difference in position and/or orientation therebetween. The difference in position may be by used the control system 112 to determine a motion of the distal tip 318. This motion may then be compared with a threshold motion value to determine whether the patient P has moved significantly.

In some embodiments, both the images 600A and 600B may be actual images. For example, the image 600A may be an image obtained before a degree of motion is detected while the image 600B may be an image obtained after that degree of motion is detected. The control system 112 may compare the images 600 with virtual views obtained from the model of the lungs 500. For example, the control system 112 may utilize the images 600 to search for matching images provided by virtual views in an area close to the distal tip 318. When matches of both the images 600 are identified, a vector between positions associated with the matched images in the model of lungs 500 may be used to identify motion of the distal tip 318. This identified motion vector may be compared with a threshold motion value in an embodiment of the operation 406 of method 400.

In some additional embodiments, more than one motion sensing modality may be used in detecting patient motion in order to improve accuracy. For example, information from both the shape sensor 314 (a first motion detecting modality) and image processing (a second motion detecting modality) may be used to determine that a patient motion has occurred. In some embodiments, thresholds may be set such that if either of two sensing modalities indicates motion, then the control system 112 takes steps to mitigate the motion. Additionally, other embodiments may include thresholds that are lower and are required to be exceeded for multiple modalities before the control system 112 identifies patient motion.

As described herein, reference is frequently made to motion of the patient P. Some embodiments of the present disclosure provide for the detection of motion of the patient P relative to the patient coordinate frame, the detection of motion of a portion of the patient P with respect to another portion (e.g., motion of the lungs relative to the trachea), and/or the detection of motion of the patient P relative to the medical system 100 itself. Some other embodiments of the present disclosure provide for the detection of motion of the patient P by detecting motion of the medical system 100 relative to the patient P. Thus, motion of the patient P as used herein may refer to relative motion between the body of the patient P and the medical instrument 104 and/or the manipulator assembly 102, regardless of whether it is the body of the patient P that moves or whether it is the medical instrument 104 or manipulator 102 that moves.

In some instances, the physician O or another person present in the vicinity of the medical instrument 104 and/or the manipulator assembly 102 may cause motion of the medical instrument 104 and/or the manipulator assembly 102. For example, the physician O may accidentally bump the instrument 104, causing motion of the distal tip of the elongate device 310. This accidental bumping of the instrument 104 may thus be interpreted by the control system 112 as patient motion. The control system 112 may automatically perform one or more operations to prevent harm from resulting from this patient motion. For example, the physician O may bump the medical instrument system 250 of FIG. 2C. The encoders at the servo joints 254 and 256 may report motion or a change in position to the control system 112. That motion would be compared with expected motion, whether in a parked state or a drive state, to determine whether or not the patient has moved. Thus, motion of components of the medical system 100 relative to patient P may be detected and responded to by the control system 112 as motion of the patient P.

Referring now to FIG. 7, an exemplary endotracheal (ET) tube 700 is illustrated as positioned within the patient P to facilitate insertion of the elongate device 310 into the lungs 500 of the patient P. A cross-sectioned portion 702 shows a portion of the elongate device 310 extending within the ET tube 700. The geometry of the ET tube 700 may be provided to the control system 112 so that a bend 704 of the ET tube 700 may be known to the control system 112. Even if a bend 704 in the tube is not precisely known, the curvature may be sufficiently distinctive to be identified in shape data as corresponding to the upper respiratory track and trachea because the portion of the elongate device 310 at the proximal end of the ET tube 700 forms a known angle (nearly 90°) with respect to the portion of the elongate device 310 at the distal end of the ET tube 700. The pose of the proximal end of the elongate device 310 may be known due to sensors extending therein, like the optical fiber shape sensor 314 in the illustrated embodiment. Based on this shape information and known curvature of the ET tube 700, the trachea of the patient P may be identified. During a medical procedure within the lungs, the trachea of the patient may be unlikely to move due to the presence of the elongate device 310. Accordingly, the portion of the elongate device 310 positioned within the ET tube 700 at any given time may be monitored in order to identify any motion of the patient P. When motion of this portion of the elongate device 310 is detected by the control system 112, the motion is likely, to be interpreted by the control system 112 as indicative of patient motion. In other words, a threshold motion value associated with the endotracheal tube 700 may be smaller than a threshold motion values used to detect patient motion at the distal tip 318 of the elongate device 310.

Some embodiments of the ET tube 700 may include a known shape feature, such as the perturbation 706 shown near the distal end of the ET tube 700. The perturbation 706 may be a small undulation or other feature that may be readily detected by the control system 112 from the shape information received from the elongate device 310. In such embodiments, the portion of the elongate device 310 disposed within the perturbation 706 may be monitored to detect patient motion as described herein. Other embodiments of the method 400 of FIG. 4 may rely on other structures in detecting motion of at least a portion of the medical instrument that is indicative of patient motion.

Returning again to FIG. 4, after motion of the portion of the medical instrument as compared with a threshold motion value or several threshold motion values, the control system 112 may generate a communication or message for rendering or presentation in the display system 110 based on the comparison performed at operation 406. At operation 408, the message may be generated and rendered in a display as shown in FIG. 8. FIG. 8 depicts an embodiment of the display system 110 which includes a rendering of a graphical user interface 800. As shown in FIG. 8, the user interface 800 includes a rendering of the lungs 500, which may be a surface model derived from preoperative or intraoperative image data or a rendering of the image data itself. A model of the elongate device 310 is also rendered in the illustrated embodiment of the user interface 800. An exemplary communication, patient motion message 802, may be overlaid on the user interface 800 to communicate to the physician O that the patient P has moved or is likely to have moved is determined by the control system 112. For example, the patient motion message 802 may include text (e.g. "Warning: patient motion detected!") and/or graphical elements to communicate to the physician O. In some embodiments, the message 802 may be displayed as a moving message or graphic across the bottom, middle, or top of a display. The patient motion message 802 may include one or more graphical user interface elements associated with options to be presented to the physician O. For example, the patient motion message 802 may include an interface element (e.g., a selectable button) associated with an option 804A whereby the physician O may request that the control system 112 discard the existing registration and perform a new registration between the lungs 500 and a model of the lungs 500. Selecting the option 804A may also comprise a request to update an existing registration. The message 802 may include displaying a numerical value (or a graphical representation of the numerical value) indicating a detected magnitude of patient motion based on sensor measurements and/or differences in sequential images. In some embodiments, the patient motion message 802 may include an interface element associated with an option 804B, the selection of which may cause the control system 112 to resume operation without updating the registration or performing a new registration.

Other communications or messages may be generated by the control system 112. For example, the control system 112 may cause the screen or an element on the screen to flash or pulse. The message may include a sound emitted from a speaker coupled to the control system 112, such as an alarm sound or a verbal message. The message may be interactive and provide options the physician O to take some action (for example request an update to a registration or request a new registration) or to ignore the detected motion. In some implementations, the control system 112 may ignore or filter out any movement commands or end effector actuation commands, until the physician O acknowledges the alert message by pushing a physical button, a virtual button, or speaks a verbal command.

Some implementations of the method 400 may include an operation that identifies a magnitude of the difference between the motion of the portion of the medical instrument and the threshold motion value or values. A threshold control value may be applied such that ignoring the patient motion message 802 by selecting the option 804B is permitted by the control system 112 only when the difference is below the threshold control value. When the difference is greater than a threshold control value, the option 804B may not be presented to the physician O. Additionally, when the difference exceeds the threshold control value, the control system 112 may alter control of the medical instrument at operation 410. For example, the control system 112 may ignore subsequent motion commands received from the master assembly 106 until a new registration is performed or an existing registration is updated. In this manner, the control system 112 may prevent the physician O from relying on a registration that is likely to be unreliable due to a relatively large motion of the patient P or of the medical system 100.

Similarly, any commands associated with the performance of a treatment, such as the performance of a biopsy with a biopsy needle protruding from the distal tip 318, may be ignored until a reliable registration is provided to compensate for the motion of the patient P.

FIG. 9 is a flowchart of a method 900 for monitoring patient movement during a medical procedure according to some embodiments. FIG. 9 depicts the method 900 as a series or sequence of operations. Embodiments of the method may include additional or alternative operations before, after, in between, or as part of the enumerated operations. Some embodiments of the method 900 may include computer-readable instructions or programming that, when executed by a processor of the control system 112, the processor causes the operations to be performed or implemented to improve the monitoring of patient movement during a medical procedure.

The illustrated embodiment of the method 900 begins at operation 902, in which the processing device of a control system generates a first model of the medical instrument, also referred to as a current measured model. The first model may correspond to the medical instrument at a first insertion position of the anatomy. In one embodiment, the first model may be understood as characterizing the current measured state of the medical instrument. In some instances, the first model of the medical instrument may be understood as a set of data that represents the state (e.g., pose, shape, or motion) of the medical instrument, which may include the elongate device 202 of FIGS. 2A and 2B, as well as the manipulator 252 of FIG. 2C, and/or the carriage 306 and insertion stage 308 of FIGS. 3A and 3B. The set of data may include measured data associated with points along the length of a catheter. As an example, the first model of the medical instrument may be generated by the control system 112 using data from a rotational or translational sensor indicative of a rotational or translational position, velocity, or acceleration of a capstan, rotational drive element, or linear drive element in the drive unit 204 or in manipulator assembly 102 of FIG. 2. As another example, the control system 112 may use tension sensors that monitor the tension on cables extending through a medical instrument to control a distal end thereof. As another example, the control system 112 may use data from the joint sensors described with respect to the medical instrument system 250 of FIG. 2C. The data from the joint sensors may be combined with known component lengths in the control arm of manipulator 252 and/or of the length of the flexible body 216 to generate a model of the medical instrument. Alternatively or additionally, the control system may use a fiber optic shape sensor, like the shape sensor 314 of FIGS. 3A and 3B, or a set of electromagnetic coils disposed at positions along the length of the medical instrument to generate at least some of the data used in producing the first model. In some instances, the first model of the medical instrument may model all of the moving components of a medical instrument system, such that the medical instrument can be fully modeled in a known reference frame. In some instances, the first model may describe only a portion of the medical instrument. For example, only the distal end 218 of the flexible body 216 of the elongate device 202 (FIGS. 2A and 2B) is included in the first model in some embodiments. In some embodiments, the data may be captured for a portion of the medical device that is in a measurement zone established by locations in anatomy. That measurement zone may be based on an insertion depth within the anatomy such as a landmark and a set retraction or insertion distance from that landmark. In a particular example, the measurement zone may include the main carina and/or areas within a particular distance proximal to the carina in the trachea. The measurement zone may be determined during registration. In an example, a retraction distance within the trachea proximally from the carina may be defined. When the carina is determined, the insertion depth is recorded and then the measurement zone is established as a fixed distance in the retraction direction as identified by the insertion axis encoder. The data is measured for the section of the catheter that is within that measurement zone. In some embodiments, the measurement zone is determined based on an endotracheal tube of the elongate instrument of an anti-bucking guide of the elongate instrument.

At operation 904, a processing device generates a second model of the medical instrument. The second model may be produced by the control system 112 and may be based on a different data source than the first model, a subset of the sources incorporated in the first model, or a combination of the different data source and the subset of the sources incorporated in the first model. In this example, the second model may be understood as characterizing a predicted state (e.g., pose, shape, or motion) of the medical instrument, and is also referred to as a predicted model.

As described in connection with method 900, the second model is a predicted model that indicates what the expected state (e.g., pose, shape, or motion) of the first model given certain assumptions. The assumptions may include many factors, such as the measured state of the medical instrument at one or more previous times. The measured state of the medical instrument at the one or more previous times may be measured at the one or more previous times and recorded by the processing device. The underlying assumptions may further include data from one or more rotational or translational sensors in the drive unit 204 of FIG. 2 at the current time. The underlying assumptions may include a combination of assumptions. For example, the second model may combine the measured state(s) (e.g. using one or more corresponding reference models) of the medical instrument with the data from one or more rotational or translational sensors (such as insertion) in the drive unit 204 of FIG. 2 at the current time.

As illustrated in FIG. 9, in some embodiments, operation 904 includes operation 905A-1, where a processing device generates a first reference model of the medical instrument based on the measured state of the medical instrument at a first reference insertion position. The first reference insertion position of operation 905A-1 may be the same as or different from the first insertion position of operation 902. The operation 904 further includes operation 905A-2, where a processing device generates a second reference model of the medical instrument based on the measured state of the medical instrument at a second reference insertion position. The second reference insertion position of operation 905A-2 may be the same as or different from the first reference insertion position of operation 905A-1 and/or first insertion position of operation 902. The measured states of the medical instrument of operations 905A-1 and 905A-2 may be measured at a time (also referred to as a previous time) before a time (also referred to as current time) of operation 902. It is noted that while two reference models from operations 905A-1 and 905A-2 are described, operation 904 may include operations to generate any number (e.g., one, two, . . . , N) of reference models associated with reference insertion positions that are the same as or different from each other.

In some embodiments, operation 904 includes operation 905B, where a processing device generates the predicted model of the medical instrument (e.g., at the first insertion position of operation 902) based on the one or more reference models of operations 905A-1 and 905A-2. For example, the predicted model may be generated using the first insertion position of the first model of operation 902 and/or the reference insertion positions of reference models of operations 905A-1 and 905A-2. In some embodiments, the predicted model may include a probability distribution of the possible expected state of the medical instrument, including for example, a mean and a standard deviation.

The time separation between the "current time" and the "previous time" may be short, e.g. milliseconds or seconds, but may also be longer. For example, the previous time may be the last time a registration algorithm was performed, which could be measured on the order of minutes. The assumptions may further include knowledge of the mechanical behavior of the medical instrument, for example the expected motion of the distal end of the flexible body 216 of the elongate device 202 based on measured motion of the proximal end. This expected motion may be based on the physical dimensions and properties of the components that make up the elongate device 218, in addition to the measured motion of the proximal end. The underlying assumptions may further include knowledge of the tissues of the patient P that provide the environment surrounding the medical instrument when in use. For example, CT scans may be segmented and processed to categorize the tissue types around the work site and to define their dimensions. The control system 112 may include a table of physical properties associated with each of the tissue types and may use a three-dimensional model of patient anatomy and the physical properties of the tissue types in order to predict how the tissue will affect the medical instrument. For example, the patient anatomy may push on the medical instrument in one direction or another such that the control system 112 predicts a location of the pushed portion of the medical instrument based on the anatomy and its properties, e.g., its propensity to push the medical instrument in a particular direction with a particular force.

At operation 906, the control system 112 compares the state (e.g., pose, shape, or motion) of the first model (e.g., generated at operation 902) and the predicted model (e.g., generated at operation 904). In some embodiments, the operation 906 may include a comparison of only a segment (e.g., a measurement zone) of the medical instrument, such as a segment extending through an endotracheal tube (ET tube) or laryngeal mask airway (LMA) or a segment of the medical instrument extending within the trachea of the patient P. Referring to the examples of FIGS. 10A through 10F, graphical representations of first model, reference model, and predicted model are illustrated. The examples of FIGS. 10A, 10B, and 10C illustrate that a difference between the first model and predicted model is below a particular threshold (e.g., for determining a patient movement). In the examples of FIGS. 10D, 10E, and 10F illustrate that a difference between the first model and predicted model is above a particular threshold (e.g., for determining a patient movement).

Referring now to FIGS. 10A and 10B, shown therein are graphical representations of system configurations with a medical instrument positioned within patient anatomy. Each of the models 1000 includes several components, which may be present or absent in the varying embodiments provided herein. FIG. 10C shows a graphical representation of a first model 1010 (also referred to as measured model 1010), and an exemplary predicted model 1012.

In the example of FIG. 10A, a first configuration 1000A includes a first component 1002, a second component 1004, and a third component 1006. The first component 1002 represents a manipulator like the manipulator 252, having rigid segments connected by joints. The second component 1004 represents an insertion stage, like the insertion stage 308 of FIGS. 3A and 3B. The second component 1004 may be coupled to the first component 1002 in a fixed manner or by a hinge having a sensor thereon such that the relationship between the component 1002 and 1004 is known to the control system 112. The third component 1006 represents a medical instrument with a flexible body, like the flexible body 216 of the elongate device 202 shown in FIGS. 2A and 2B. The flexible body of the third component 1006 may be coupled to the second component 1004 by a backend mechanism and may have a fixed or measured orientation with respect to the backend mechanism. The third component 1006 may further include a shape sensing system, such as a fiber-optic shape sensor or a series of electromagnetic sensors. By querying sensors distributed from the proximal end of the medical instrument to the distal end thereof, a set of data points along the length of the medical instrument may be collected and used to determine and store lengths and other geometric information associated with the included components, the state (e.g., pose, shape, or motion) of the medical instrument may be measured and modeled by the control system 112. Additionally, the control system 112 may query tens, hundreds, or thousands of times a second to be able to measure motion of the medical instrument.

Similarly, a reference configuration 1000B includes a first component 1002, a second component 1004, and a third component 1006. The reference configuration 1000B may be substantially similar to the first configuration 1000A, except that the reference configuration 1000B is generated based on a measured state of the medical instrument at a time (e.g., previous time) different from a time (e.g., current time) associated with the first configuration 1000A. In the example of FIGS. 10A and 10B, the first configuration 1000A is associated with a first insertion position, the reference configuration 1000B is associated with a reference insertion position, and there is a distance D1 between the first insertion position and the reference insertion position. In the examples of FIGS. 10A and 10B, the components 1002 and 1002B and the components 1004A and 1004B have substantially similar poses. FIGS. 10A and 10B show the models 1000A and 1000B, according to some embodiments. Between these two figures, the position of the back end mechanism on the component 1004A and 1004B has changed. The movement D1 of the backend mechanism results in the retraction of the flexible component modeled as 1006A and 1006B.

As shown in FIG. 10C, the control system 112 may perform a comparison of multiple models including for example a predicted model 1012 and a first model 1010. The first model 1010 and the predicted model 1012 can each be generated based on data representing the shape of the medical instrument 1006 within a specified zone, such as a measurement zone 1008, each taken at different times and/or different insertion distances.

The first model first model 1010 may be generated from one or more current states or one or more currently measured models, for example, taken during the system configuration 1000A.

The predicted model 1012 may be generated from one or more previous states or one or more previously measured models, for example taken during the system configuration 1000B (e.g., reference configurations associated with reference models of operation 905A-1 and 905A-2), and one or more commands received from an operator while the medical instrument was in the previous state, such as an insertion command for an insertion distance. For example, the predicted model 1012 may be generated using the previous position of the backend mechanism of reference configuration 1000B, and knowledge of the input commands and actuator commands received, issued, and implemented in connection with the movement D1. The predicted model 1012 may further include state information, such as input received from the user that described a desired motion to be implemented by actuators. The input may be defined in terms of the manipulation of an input device, such as the master assembly 106, and/or as the translation of that into control signals for actuators such as a capstan that applies tension on a cable in order to move or otherwise actuate the medical instrument. While FIG. 10C illustrates a predicted model 1012 associated with the third component 1006 in the measurement zone 1008, in various embodiments, the predicted model 1012 may also be associated with the entire length of the third component 1006, e.g., using data for the entire length of the catheter.

Additionally, as noted herein the predicted model 1012 may further be based on anatomical information or other information that characterizes the surrounding environment of the medical instrument, such as tissue that is pushing against a portion of the medical instrument. Additionally, the predicted model may use data from the user input device. For example, if the user commands the system through the input device to bend left, the predicted model would show the catheter bending left in its prediction. In some instances, the predicted model would include the predicted result of movement commands included in state information characterizing the reference models of operation 905A-1 and 905A-2. For example, the reference models of operation 905A-1 and 905A-2 may include the actual configuration of the medical instrument resulting from a movement command and/or the movement command itself, while the predicted model 1012 includes the predicted configuration of the medical instrument based on the movement command. The control system 112 may detect differences in the actual configuration and the predicted configuration.

In some embodiments, the measured model 1010 generated from the first configuration 1000A and the predicted model 1012 generated at least in part from reference configuration 1000B (and its corresponding reference model) have substantially overlapping shapes within the measurement zone 1008, but differ in shape at the proximal and distance ends. Comparisons may include all components of the measured model 1010 and predicted model 1012 or a subset thereof. In some embodiments, as shown in FIG. 10C, the comparison may be based on a measured model 1010 and a predicted model 1012, in the measurement zone 1008, ignoring the components 1002 and 1004. In the example of FIG. 10C, measured model 1010 and predicted model 1012 substantially overlap with each other. Thus, in the example of FIG. 10C, it is determined that there is no patient movement because the difference between measured model 1010 and predicted model 1012 is less than a particular threshold.

Referring to the examples of FIGS. 10D, 10E, and 10F, a difference in position of patient anatomy is illustrated, resulting in a difference between a first model and predicted model above a particular threshold (e.g., for determining a patient movement). FIGS. 10D and 10E illustrate graphical representations of a first system configuration 1000D and a reference system configuration 1000E. FIG. 10F illustrates an exemplary comparison of a first model 1010 (e.g., generated from first system configuration 1000D) and a predicted model 1012 (e.g., generated from reference model generated from reference configuration 1000E). The system configurations 1000D and 1000E are substantially similar to the system configurations 1000A and 1000B, while the comparison of FIG. 10F is substantially similar to the comparison of FIG. 10C, except for the differences described below. FIG. 10D illustrates a shift in patient anatomy 502. FIG. 10F shows that the first model 1010 and the predictive model 1012 diverge from each other. The comparison performed at operation 906 may identify this divergence (e.g., in terms of its magnitude and pose), between the first model 1010 and predicted model 1012. Based on this, the control system 112 may determine a current state of the instrument represented by the system configurations 1000A or 1000D, or a current state of the patient, based on the comparison, at operation 908. As described herein, the control system 112 may also determine whether the patient has moved based on the comparison and identification, at operation 910. In the example of FIG. 10F, the control system 112 may determine that the difference between measured first model 1010 and predicted model 1012 exceed a particular threshold, and thereby determine that the patient has moved.

The comparison performed at operation 906 may be a comparison of any or all of the components 1002, 1004, and 1006 or of specific portions thereof, by for example, shifting the measurement zone 1008. For example, some comparisons may include only a comparison of the portion of the component 1006 inside the anti-buckling guide 322 of FIGS. 3A and 3B. In some embodiments, different weights may be assigned to different components of the medical instrument or of different portions of the different components. For example, some embodiments of the operation 906 may include a comparison of only a segment (e.g., a measurement zone 1008) of the measured component 1006A and the predicted component 1006C, such as a segment extending through an endotracheal tube (ET tube) or laryngeal mask airway (LMA) or a segment of the medical instrument extending within the trachea of the patient h. In some instances, comparing the models may include comparison of the measured and predicted motions or shapes in a particular direction or along or away from a particular place. For example, the models may be compared based on their motion in a direction normal to the table T, in a direction parallel to the table T, or in some other direction of interest. Determining the state of the patient may include determining that the patient has moved and may include determining a type of movement of the patient, such as an identification of a cough or of normal period motion, such as respiratory motion. Alternatively or additionally, determining the state of the patient or instrument may include determining an additional component used in the medical procedure. For example, the state may indicate that the medical instrument is introduced into the patient via a particular trocar cannula, through a particular ET tube, through a particular LMA, etc. Shape information included in the state may be matched to known geometries of a plurality of such entry devices. Determining the state of the patient may also include detecting buckling of the portion of the medical instrument disposed in the anti-budding guide 322.

FIG. 11A shows a representation of the measured model 1010 and the predicted model 1012 relative to a lung L of the patient P. In some instances, such graphical representations may be provided to an operator of the medical instrument in a display, such as the display system 110 of FIG. 1. FIG. 11A shows multiple diverges along the length of the models. In some instances, the comparison may be performed at regular intervals along the lengths of the models. In some instances, only the divergences in a particular direction are noted. For example, FIG. 11B shows a side view of the models 1000A and 1000C, divergences or differences D4, D5, D6, and D7 are labeled. These divergences may be numerically represented along an axis normal to the table T.

Returning to operation 910, the control system 112 may determine whether the patient has moved based on the comparison of the measured model 1010 and the predicted model 1012. As noted, in some instances only specific segments of the model may be compared. For example, only the area around the divergence D4 in FIG. 11B may be compared in some embodiments and used to determine whether the patient P has moved. In order to determine whether the patient P has moved, the control system 112 may compare any identified divergences or differences with a threshold value. This threshold value may be different depending on the component of the models being compared or the specific portions of the models being compared. For example, when the divergence D4 is greater than 10 mm, 5 mm, or 1 mm, the control system 112 may identify the divergence D4 is indicating that the patient P has moved. In general, the divergence may be determined in many ways, such as an absolute magnitude, but also in the magnitude in a specific direction, or in terms of frequency of motion. The indication of the patient P has moved is determined relative to the medical instrument, such that a movement of the medical instrument relative to the patient (for example, the cart supporting the medical instrument may be accidentally pushed) is interpreted as patient movement. The thresholds applied in determining whether the patient P has moved may be dependent upon the approximate location of the medical instrument relative to the work site or environment surrounding the medical instrument. For example, the threshold for a divergence in the area of the trachea may be different than the threshold for a divergence in the area that is inside or likely to be inside the lungs. The threshold may also be different depending on the task being performed or the required level of accuracy. For example, the threshold may be set more stringent if the system is being used to access to a particular small region, if the target area is close to a sensitive body structure such as a vessel or the pleura, or if the nature of the tasks (for example ablation) requires more accuracy. The control system 112 may include such information and utilize it during comparison and determination operations.

In some embodiments, the difference between the measured model and the predicted model is determined by comparing the points of the measured model with the points of the predicted model (e.g., based on one or more comparison criteria). It may be determined that there is no patient movement if the difference is less than a corresponding threshold of the comparison criterion, and that there is patient movement if the difference is equal to or greater than the corresponding threshold. Various comparison criteria with corresponding thresholds may be used. In an example, the difference is based on a sum of amplitude differences between measured points of measured model 1010 and corresponding predicted points of predicted model 1012, and the corresponding threshold is a total threshold distance (e.g., 15 mm). In another example, the difference is determined using an amplitude difference (e.g., in a radial direction) and/or a length difference (e.g., in a linear direction along the insertion axis). In yet another example, the difference is determined using an average amplitude difference or a maximum amplitude difference over the entire length of the measurement zone 1008. In some examples, the amplitude is based on a maximum along the entire length of the measurement zone 1008. In yet another example, the comparison criteria provide comparison of movement properties (e.g., frequency, velocity, acceleration, etc.) and shape properties (e.g., amplitude, peak numbers, dip numbers, curvature, etc.) with corresponding threshold. In some embodiments, the comparison criteria may provide that the threshold is based on the distribution of the predicted model 1012. For example, it may be determined that there is a patient movement if the measured model 1010 in the measurement zone 1008 is outside of a standard deviation of the distribution of the predicted model 1012.

As a result of the operation 910, the control system 112 may take an action such as issuing an alert to an operator via the display system 110 and/or by altering control of the medical instrument based on the comparison and determination as shown in FIG. 9 at operation 912. In some embodiments, the control system 112 may display a patient motion message 802 as shown in FIG. 8. In some embodiments, the user may ignore or dismiss an alert or message, or may be unable to dismiss a message until an action is taken. The control system 112 may ignore, disregard, or not implement any movement commands or end effector actuation commands received from the operator until the message 802 is acknowledged or interface element options 804A and/or 804B are selected. In some embodiments, the control system 112 may actively attempt to maintain the actual location of the medical instrument or may allow the medical instrument to compliantly yield to pressures and forces applied by tissues and surrounding environment. In another embodiment, the control system may disable energy supply to an energized instrument, such as an ablation probe, that is used in the method 900 to treat a patient. Additionally, the control system 112 may instruct the user to perform a registration process or update an existing registration between the medical instrument, a model of the patient anatomy, and the actual patient anatomy when the control system determines that the patient P has moved. This is because movement of the patient P may cause an existing registration of these features to become unreliable and unsuitable for use by the operator.

Embodiments of the present disclosure may provide for the detection of patient motion using sensors disposed on structures required for the medical procedure being performed and using measured and predicted models of the pose and/or motion of the utilized medical instruments. For example, rather than use a dedicated system for monitoring motion of the patient (such as optical, EM, or fiber optic sensors) the existing sensors and systems such as the fiber optic shape sensor 314 of the elongate device 310 may be relied upon to obtain positioning, orientation, and/or shape information. This information may be primarily used by the control system 112 in characterizing the catheter for purposes of registration and use in image-guided medical procedures. As described herein such information may be used secondarily to monitor for patient motion to prevent use of unreliable registrations. In many embodiments, the systems described herein allow for such dedicated systems to be replaced, enabling more information to be obtained from fewer pieces of equipment. This can make a procedure more affordable and can remove clutter from the work site.

One of ordinary skill in the art may be able to identify combinations of disclosed embodiments and additional features that are within the scope of the present disclosure.

Accordingly, the spirit and scope of the present disclosure may be best understood by reference to the following claims.

What is claimed is:

1. A method of controlling an elongate instrument during a medical procedure involving motion of the elongate instrument relative to a patient, the method comprising:
   generating, by a control system, a measured model of the elongate instrument;
   generating, by the control system, a predicted model of the elongate instrument, wherein the predicted model indicates an expected state of the measured model, wherein generating the predicted model comprises:
      determining, by the control system, a reference pose of the elongate instrument, wherein the reference pose is based on a first set of data provided by a sensor system extending within the elongate instrument;
      determining, by the control system, an insertion distance of the elongate instrument; and
      combining, by the control system, data corresponding to the reference pose with data corresponding to the insertion distance to generate the predicted model of the elongate instrument;
   comparing, by the control system, the measured model with the predicted model; and
   determining, by the control system, whether the patient has moved relative to the elongate instrument based on the comparison.

2. The method of claim 1, wherein the measured model is based on a measured pose of the elongate instrument, and wherein the measured pose and the reference pose are each based on data provided by the sensor system, wherein the sensor system includes a shape sensor extending along a length of the elongate instrument.

3. The method of claim 1, wherein the determining whether the patient has moved relative to the elongate instrument further comprises:
   determining, by the control system, whether the patient has moved relative to the elongate instrument based on the comparison and a threshold associated with the comparison.

4. A medical system comprising:
   an elongate instrument including a sensor system extending therein;
   a control system in communication with the sensor system to measure a pose of the elongate instrument, the control system adapted to perform operations comprising:
      generating a measured model of the elongate instrument;
      generating a predicted model of the elongate instrument, wherein the predicted model indicates an expected state of the measured model, wherein generating the predicted model comprises:
         determining a reference pose of the elongate instrument, wherein the reference pose is based on a first set of data provided by the sensor system of the elongate instrument;
         determining an insertion distance of the elongate instrument; and
         combining data corresponding to the reference pose with data corresponding to the insertion distance to generate the predicted model of the elongate instrument;
      comparing the measured model with the predicted model; and
      determining whether a patient has moved relative to the elongate instrument based on the comparison.

5. The medical system of claim 4, wherein the elongate instrument includes a flexible component, and wherein the sensor system extends within the flexible component.

6. The medical system of claim 4, wherein the sensor system includes a shape sensor including a fiber optic shape sensor or a plurality of electromagnetic (EM) sensors.

7. The medical system of claim 6, wherein the measured model is based on a measured pose of the elongate instrument.

8. The medical system of claim 7, wherein the measured pose and the reference pose are each based on shape data from the shape sensor of the sensor system of the elongate instrument.

9. The medical system of claim 8, wherein the shape data provided by the shape sensor is received from a segment of the elongate instrument positioned in a measurement zone.

10. The medical system of claim 9, wherein the measurement zone corresponds to a segment of an endotracheal tube or a segment of a trachea of a patient, and wherein the elongate instrument is positioned relative to the patient.

11. The medical system of claim 4, further comprising a robotic assembly including a second sensor system disposed along the robotic assembly, wherein the elongate instrument is coupled to the robotic assembly and wherein the control system is in communication with the second sensor system.

12. The medical system of claim 11, wherein the robotic assembly includes at least one of an insertion stage, a manipulator, or a robotic arm.

13. The medical system of claim 11, wherein the insertion distance is measured by the second sensor system.

14. The medical system of claim 11, wherein the second sensor system includes a rotational encoder or a linear encoder.

15. The medical system of claim 11, further comprising an input control device, wherein the control system is in communication with the input control device and the robotic assembly to control the insertion distance of the elongate instrument and wherein the insertion distance is based on one or more commands received from the input control device.

16. The medical system of claim 4, wherein the determining whether the patient has moved relative to the elongate instrument further comprises:
   determining whether the patient has moved relative to the elongate instrument based on the comparison and a threshold associated with the comparison.

17. The medical system of claim 4, wherein the predicted model includes a probability distribution based on a plurality of possible expected states of the elongate instrument.

18. The medical system of claim 4, further comprising a display system for displaying a message based on the determining whether the patient has moved relative to the elongate instrument.

19. The medical system of claim 4, wherein if a determination is made that the patient has moved relative to the elongate instrument, determining whether the patient has moved further comprises determining a type of movement of the patient.

20. The medical system of claim 4, wherein comparing the measured model with the predicted model comprises comparing the measured model with the predicted model in a direction normal to an operating table or in a direction parallel to the operating table.

* * * * *

UNITED STATES PATENT AND TRADEMARK OFFICE
CERTIFICATE OF CORRECTION

Page 1 of 1

PATENT NO. : 12,004,830 B2
APPLICATION NO. : 16/638660
DATED : June 11, 2024
INVENTOR(S) : Troy K. Adebar and Vincent Duindam It is certified that error appears in the above-identified patent and that said Letters Patent is hereby corrected as shown below:

In the Specification

Column 22, Line 41, change "patient h" to -- patient P --

Column 22, Line 62, change "anti-budding" to -- anti-buckling --

Column 22, Line 67, change "HA" to -- 11A --

Signed and Sealed this
Thirteenth Day of August, 2024

Katherine Kelly Vidal
*Director of the United States Patent and Trademark Office*